United States Patent [19]
Strauss et al.

[11] Patent Number: 5,837,905
[45] Date of Patent: Nov. 17, 1998

[54] CARDIOPLEGIA MONITORING SYSTEM, FLOW CELL CASSETTE, VARIABLE RATIO VALVE, AND METHOD

[75] Inventors: Brian Strauss, Mission Viejo; George W. White, Lake Forest; Kenneth M. Galt, Seal Beach, all of Calif.

[73] Assignee: Gish Biomedical, Inc., Irvine, Calif.

[21] Appl. No.: 690,259

[22] Filed: Jul. 24, 1996

[51] Int. Cl.⁶ .................................................. A61M 37/00
[52] U.S. Cl. ............................................ 73/861.63; 604/4
[58] Field of Search ................................ 73/861.63, 727, 73/706, 721, 726; 128/672, 675, 691, 748; 604/4

[56] References Cited

U.S. PATENT DOCUMENTS

| | | | |
|---|---|---|---|
| 3,592,187 | 7/1971 | Youdin et al. | 128/691 |
| 3,981,197 | 9/1976 | Lieber et al. | 73/727 |
| 4,226,124 | 10/1980 | Kersten | 128/748 |
| 4,252,126 | 2/1981 | Mandl | 128/748 X |
| 4,401,431 | 8/1983 | Arp . | |
| 4,416,280 | 11/1983 | Carpenter et al. . | |
| 4,535,635 | 8/1985 | Claren et al. | 73/726 X |
| 4,610,256 | 9/1986 | Wallace et al. | 73/721 X |
| 4,883,455 | 11/1989 | Leonard . | |
| 5,322,500 | 6/1994 | Johnson et al. . | |
| 5,466,216 | 11/1995 | Brown et al. . | |

Primary Examiner—George M. Dombroske
Assistant Examiner—Paul D. Amrozowicz
Attorney, Agent, or Firm—George F. Bethel; Patience K. Bethel

[57] ABSTRACT

A system and method for delivery of cardioplegic solution to the heart of a patient incorporates novel venturi flow cells individually adapted for insertion in the blood and crystalloid solution lines together with transducers for measuring a pressure drop across each venturi flow cell and transmitting it to a microprocessor to calculate flow rate for display on a monitor. The novel self-venting and self-priming transducers and venturi flow cells are incorporated in a disposable cassette. The transducers in the disposable cassette are removably snap connected to a hand set or plug housing which communicates with the computer or microprocessor and monitor. A novel variable ratio valve permits infinitely variable ratios of blood and crystalloid solution.

8 Claims, 16 Drawing Sheets

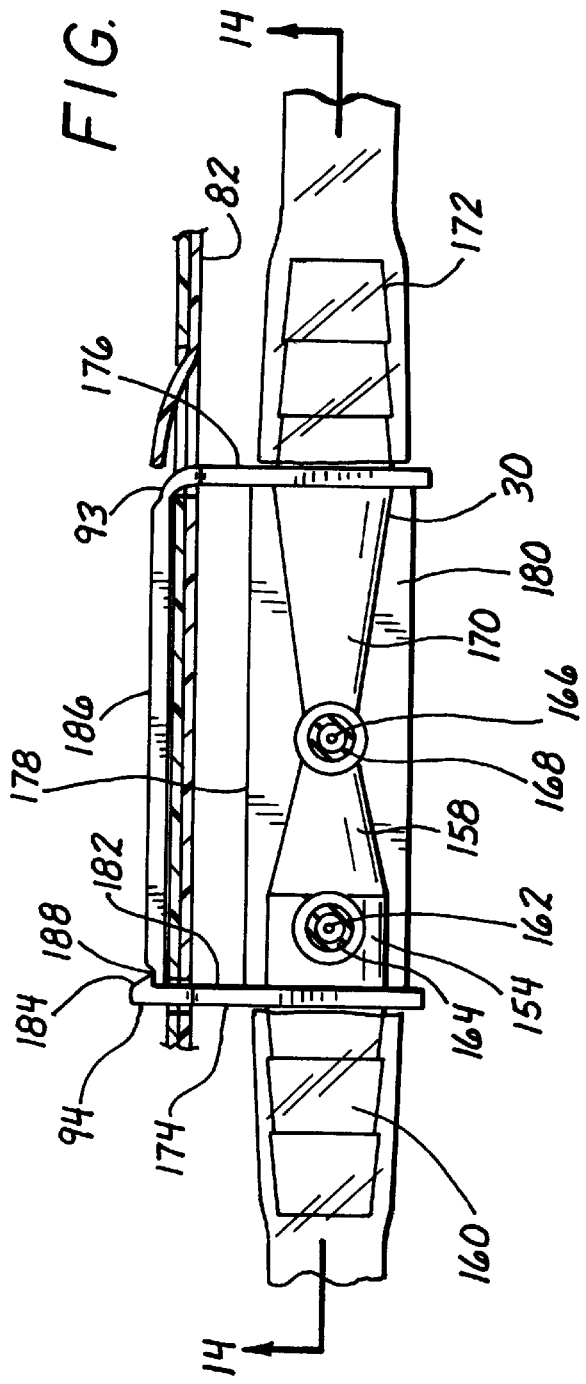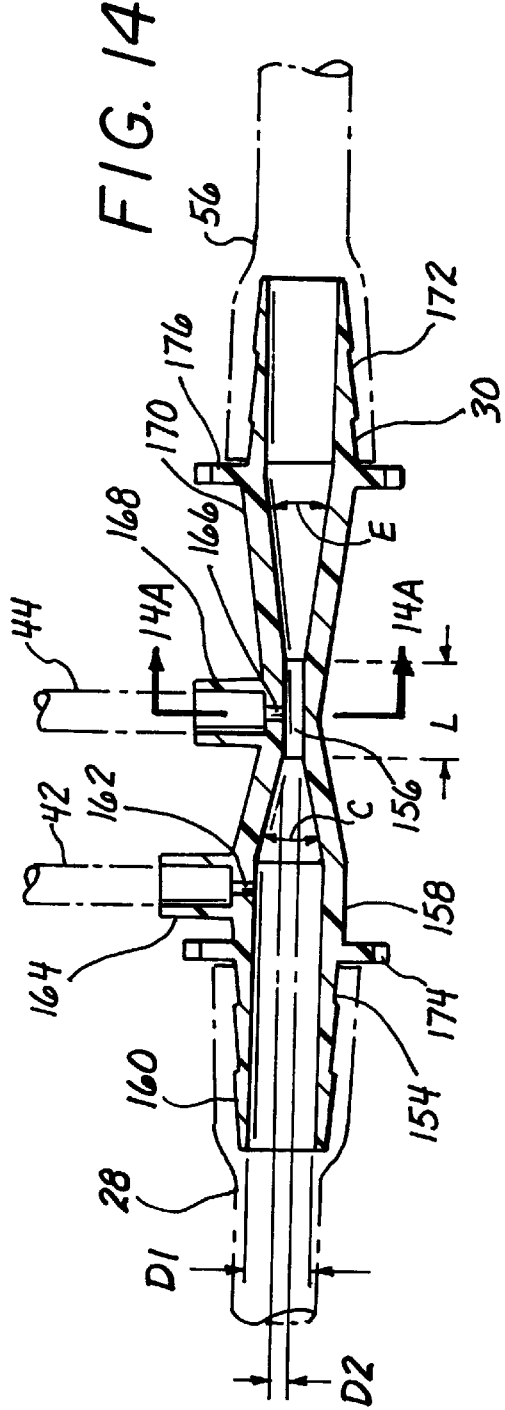

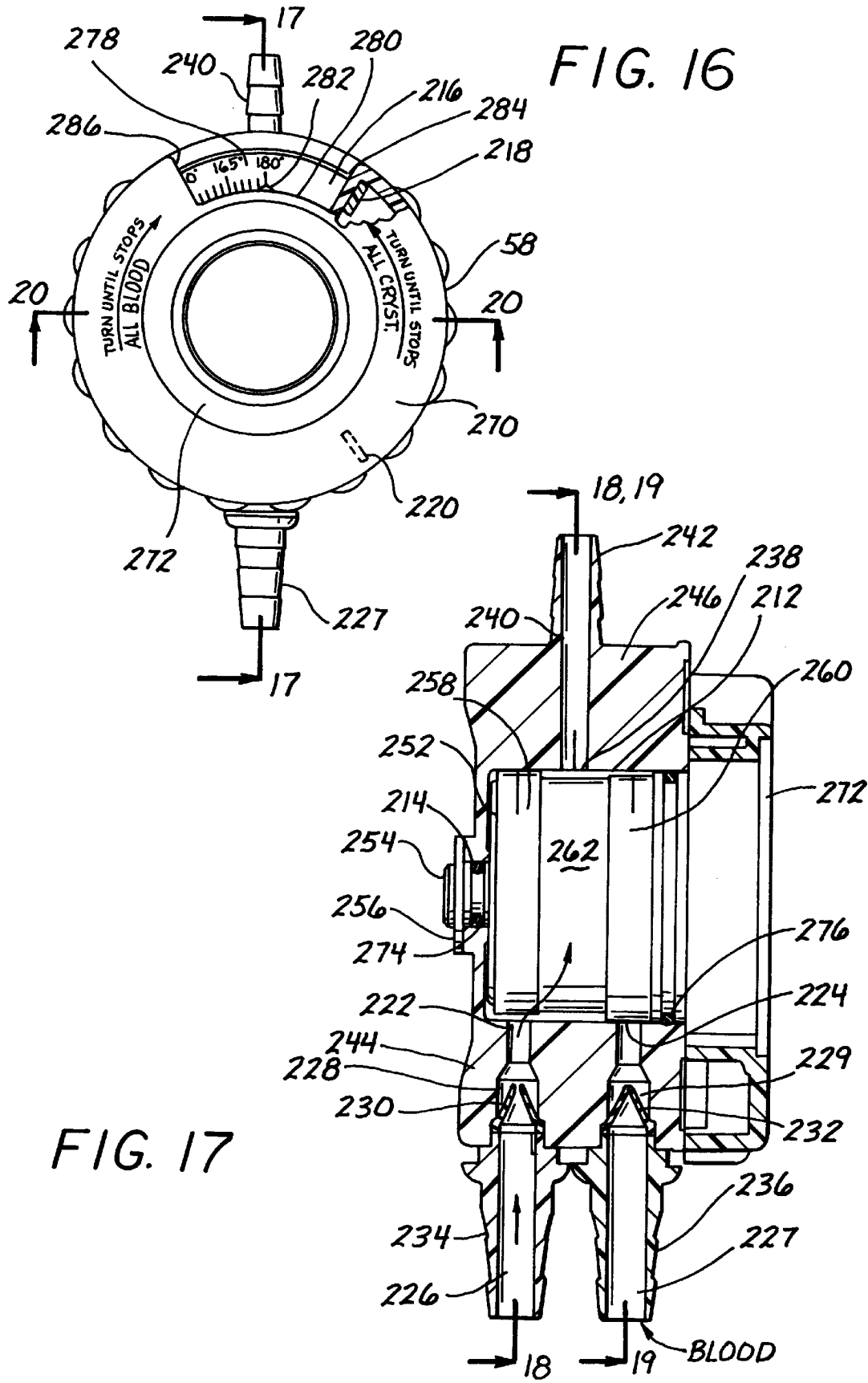

CARDIOPLEGIA MONITORING SYSTEM, FLOW CELL CASSETTE, VARIABLE RATIO VALVE, AND METHOD

FIELD OF THE INVENTION

This invention relates to the field of open heart surgery and particularly to a venturi flow cell and transducer cassette, a venturi flow cell for blood, a venturi flow cell for crystalloid solution, a transducer, a variable ratio valve, a method for measuring blood or crystalloid flow, a system and method for delivery of cardioplegic solution to the heart.

BACKGROUND OF THE INVENTION

During open heart surgery, the heart muscle or myocardium requires vital oxygen and energy supplements during the surgical procedure to prevent deterioration of the myocardium. In order for the surgeon to work on the heart, it must be stopped. This is accomplished by means of a cardioplegic solution or crystalloid which contains potassium chloride (KCL) in an aqueous solution which interferes with the electrical activity of the myocardium on a cellular level. Crystalloid defines a substance that forms a true solution, in solution diffuses readily through a membrane, and is capable of being crystallized. Crystalloid and crystalloid solution are used interchangeably throughout this application.

In cardiovascular bypass, blood from the vena cava of a patient undergoing coronary surgery is sent to a venous reservoir and is passed through an oxygenator or artificial lung where it is mixed with oxygen. A major portion of this oxygenated blood is filtered and returned to the patient for circulation throughout the body to be returned again and gathered from the vena cava.

In order to initiate cardioplegia, a minor portion of the oxygenated blood is withdrawn from the oxygenator and is then mixed in specific ratios with the potassium chloride or other cardioplegic solution. The mixture is then passed through a heat exchanger. Then the mixture is intermittently or continuously perfused to the myocardium, usually via the aortic root or the coronary sinus. In some instances, all blood or all cardioplegic solution is perfused to the heart.

Blood and cardioplegic solution that seeps out of the left ventricle and surrounding tissue is collected from the chest or pleural area for reuse. There are several suction devices which collect the blood and other fluids from the pleura.

If the blood is of high quality it is sent to the venous reservoir for filtration and oxygenation. If the blood is of good quality but is dilute or is mixed with cardioplegic solution, it is suctioned off to a cell saver which operates like a centrifuge to separate the good quality blood cells from the excess cardioplegic solution for reuse.

There are two main types of cardioplegia: cold cardioplegia and warm cardioplegia, the choice of which is determined by the surgeon depending upon the condition of the patient and the type of surgery.

Cold cardioplegia utilizes a cold (about 4°–12° C. cardioplegic solution comprised of 100% crystalloid solution or a mixture of cardioplegic solution and blood with hypothermia to reduce the energy required by the heart. The solution or mixture is infused intermittently or continuously throughout the cardiac surgery.

Warm cardioplegia utilizes a mixture of oxygenated blood and a cardioplegic solution at a temperature of about 18°–37° C. The mixture is infused continuously or intermittently throughout the cardiac surgery.

Using cold or warm cardioplegia, the mixture of the blood and the cardioplegic solution is carefully controlled. Normally, there is a 4 to 1 ratio of blood to cardioplegic solution although ratios of 1 to 1, 2 to 1, and 9 to 1 ratio are sometimes used. The ratio can be controlled by the diameter of the tubing used to carry the blood (typically ¼ inch diameter tubing) and the diameter of the tubing used to carry the cardioplegic solution (typically ⅛ inch diameter tubing). The maximum ratio of blood to cardioplegic solution is then partially fixed by the diameter of the tubing.

The fixed ratio of the blood to the cardioplegic solution maintains a constant amount of potassium given to the heart. This can result in potassium overloading which is thought to cause damage to the myocardium.

In order to overcome this problem, two or more separate bags of cardioplegic solution can be used which contain different concentrations of potassium. One bag having a high concentration of potassium is used to arrest the heart and the other bag containing a lesser concentration of potassium is used to maintain the heart.

The two or more separate sources or bags of cardioplegic solution are connected to a Y fitting. A clamping means permits the selection of one or the other bag of cardioplegic solution for mixture with blood.

The two respective tubing lines containing the cardioplegic solution and the blood are passed in parallel through a pump such as a roller pump. The two respective tubing lines then pass through a mixing device having a single exit line. The pump delivers the mixture at a specific preset flow rate to an antegrade/retrograde valve for infusion to the heart.

Infusion is normally conducted at a relatively high flow rate to the aortic root (antegrade infusion) to arrest the heart. Alternate infusion is made at a lower flow rate to the coronary sinus (retrograde infusion) and to the aortic root thereafter.

Cardioplegic solution consists of aqueous solutions of potassium chloride and often contains additional ingredients such as dextrose, glutamate, aspartate, and various other electrolytes such as $Ca^{+2}$ and $Mg^{+2}$. Cardioplegic solutions are delivered by alternating between antegrade cardioplegia and retrograde cardioplegia containing high and low potassium concentrations.

In order to arrest the heart and to limit the total cardioplegia volume, typically antegrade cardioplegia is given first to the aortic root to supply approximately 20 mEq/L of potassium given at 300–350 ml/min for 2 minutes to stop the heart. Thereafter, retrograde cardioplegia is delivered to the coronary sinus at 100–200 ml/min to supply approximately 10 mEq/L of potassium for about 2 minutes. In this instance, the concentration of potassium is controlled through the flow rate.

Alternately, the high concentration potassium chloride cardioplegic solution can be infused antegrade to arrest the heart. Then, the low potassium cardioplegic solution can be infused to deliver the balance of the potassium.

Thereafter, reinfusions during surgery are divided between 1 minute antegrade and 1 minute retrograde at approximately 20 minute intervals. Reinfusions can also be delivered continuously.

Warm reinfusion is often given prior to restarting the heart. For example, warm reinfusion is delivered at 150 ml/min for 3–5 minutes which is divided between antegrade and retrograde to limit reinfusion injury.

Other combinations of cold and warm cardioplegia are utilized depending upon the individual surgeon and the condition of the patient. This invention should not be limited by the various combinations of delivery of cardioplegia used or by the exact combination of ingredients.

It is desirable to know precisely how much KCl is being delivered as well as to track the total amount of KCl which has been delivered to the patient to avoid delivery of excessive amounts.

Antegrade pressure at the aortic root should be maintained at less than about 300 mm Hg pressure and retrograde pressure at the coronary sinus should be maintained at less than about 50 mm Hg pressure to avoid myocardial edema and hemorrhage.

The significant pressure differential requires accurate pressure reading and control. In addition, it is necessary to ensure that the proper pressure is delivered to the aortic root or to the coronary sinus to avoid damage to the heart. Pressure can be controlled by adjustment of the flow rate of the pump. Similarly, the temperature must be monitored and controlled.

Since the antegrade cardioplegic solution and the retrograde cardioplegic solution are introduced into different parts of the heart at different times, two lines or tubes are required. The two lines are connected to a roller or other type of pump. One of the lines must be clamped or otherwise restricted while the other is in operation.

One device which has been used in the past to stop the flow in one line while permitting flow in the other line is in the form of a three way stopcock which selectively permits flow through one or both lines depending on its position.

The three way stopcock device requires two hands for operation making it inconvenient to operate. The stopcock is connected to PVC tubing which gives good visibility but kinking and leaks of the tubing have been experienced. Also, there is possible pressurization of the coronary sinus via communication with the antegrade pressure monitoring line.

Another device utilizes a rotary compression switch and silicone rubber delivery lines. Both lines pass through a housing, one on either side of a circular rotation member which selectively compresses or releases one or both lines depending upon the position of rotation. Thus, both lines can be unclamped in order to prime the lines, and then one line clamped to permit selective flow in the other line, or both lines can be clamped to prevent flow through either line.

There are several disadvantages to the use of the rotary clamping switch. One disadvantage is that two hands must be used to change the position of the switch.

The ratio of cardioplegia solution to blood is fixed by the above described clamping switches. Most desirably, the ratio of cardioplegia to blood is infinitely variable so that all blood or all cardioplegia solution or any ratio in between can be administered to a patient.

Also, the delivery system should avoid creating shear forces great enough to cause red cell destruction or hemolysis.

The above disadvantages are eliminated by the system, venturi flow cells, transducer assembly, and variable ratio valve, and method of the invention.

SUMMARY OF THE INVENTION

The venturi flow cells and transducer assembly, variable ratio valve, monitoring system and method of the invention solve many of the disadvantages of the prior art devices. In particular, a venturi flow cell and transducer assembly contains two novel venturi flow cells individually adapted for insertion in the blood and crystalloid solution lines together with transducers for measuring a pressure drop across each venturi flow cell and transmitting it to a microprocessor. A variable ratio valve permits infinitely variable combinations or ratios of blood and crystalloid solution.

Each venturi flow cell provides the mechanical differential pressure to the corresponding pressure transducer when there is flow through the crystalloid solution line and flow through the blood line. The differential pressure taken with the cross sectional area of the venturi flow cells allows the microprocessor to calculate a flow rate using the Venturi principle equation to measure the rate of flow and pressure of blood and crystalloid solution.

The venturi flow cell for crystalloid is differently sized from the venturi flow cell for blood in order to optimize the flow characteristics of the two different fluids through the venturi throat or constricted portion. This is necessary to ensure that a pressure drop across the throat or constriction of each venturi flow cell would be sufficient to permit detection with high definition pressure monitoring equipment.

Another important consideration was to avoid creating shear forces which would cause destruction of red blood cells, i.e. hemolysis. Thus, the differences between the venturi flow cells are mainly in the diameter and length of the venturi throat or constriction.

The variable ratio valve is manually operated by the perfusionist to give any desired ratio of blood to crystalloid solution over an infinite range. As a consequence, the variable ratio valve allows for adjustment of the ratio of blood to crystalloid solution at various flow rates. Both the ratio and the volume of blood and crystalloid solution can be controlled.

The venturi flow cells and transducer assembly has novel, quick priming, auto or self-venting transducers which transmit the rates of flow and pressure of blood and crystalloid solution to a computer or microprocessor which converts the signal to one or more visual display screens on a monitor.

The transducer assembly further includes a disposable cassette containing the venturi flow cells which are interconnected to transducers. The transducers are removably snap connected to a hand set or plug housing which communicates with the computer or microprocessor and monitor.

Since the blood and crystalloid solution are not in contact with the plug housing, it is reusable while the disposable cassette is replaced for each patient.

The monitoring system also includes a temperature probe which generates a signal which is sent to the computer or microprocessor for display on the monitor.

The monitor display shows the crystalloid flow rate and the blood flow rate, the ratio of the blood to crystalloid flow as determined by the variable ratio valve and measured by the transducers. This information is constantly being updated and displayed on the monitor display screen.

In addition, the monitor displays the pressure of antegrade infusion flow, the pressure of retrograde infusion flow, and cardioplegic solution temperature. If the pressure exceeds preestablished limits, an alarm will sound.

Other measurements which can be displayed on the monitor include among others, intermittent cardioplegia flow, dynamic KCl/L of solution being infused, the accumulated volume of the total cardioplegia solution infused, the accumulated volume of each bag of crystalloid solution infused, and the accumulated KCl and substrates.

Also displayed are low battery condition, the pause time interval between pump infusions, which bag of crystalloid solution is being used and that bag's parameters that are being used for bag concentration dependent calculations. The total elapsed time of the surgery is also displayed. Some of these figures require input by the user into the monitor. Other measurements are also displayed which are further explained in more detail.

BRIEF DESCRIPTION OF THE DRAWINGS

The invention will be more readily understood by the description which follows taken in conjunction with the attached drawings briefly described below.

FIG. 13 shows a section through the venturi flow cell for blood taken along the lines 13—13 of FIG. 8.

FIG. 14 shows an axial section of the venturi flow cell for blood taken along the lines 14—14 of FIG. 13.

FIG. 16 shows a front view of the variable ratio valve of the invention.

FIG. 17 shows a section through the valve of FIG. 16 taken along the lines 17—17.

DETAILED DESCRIPTION OF THE INVENTION

Figure 1:
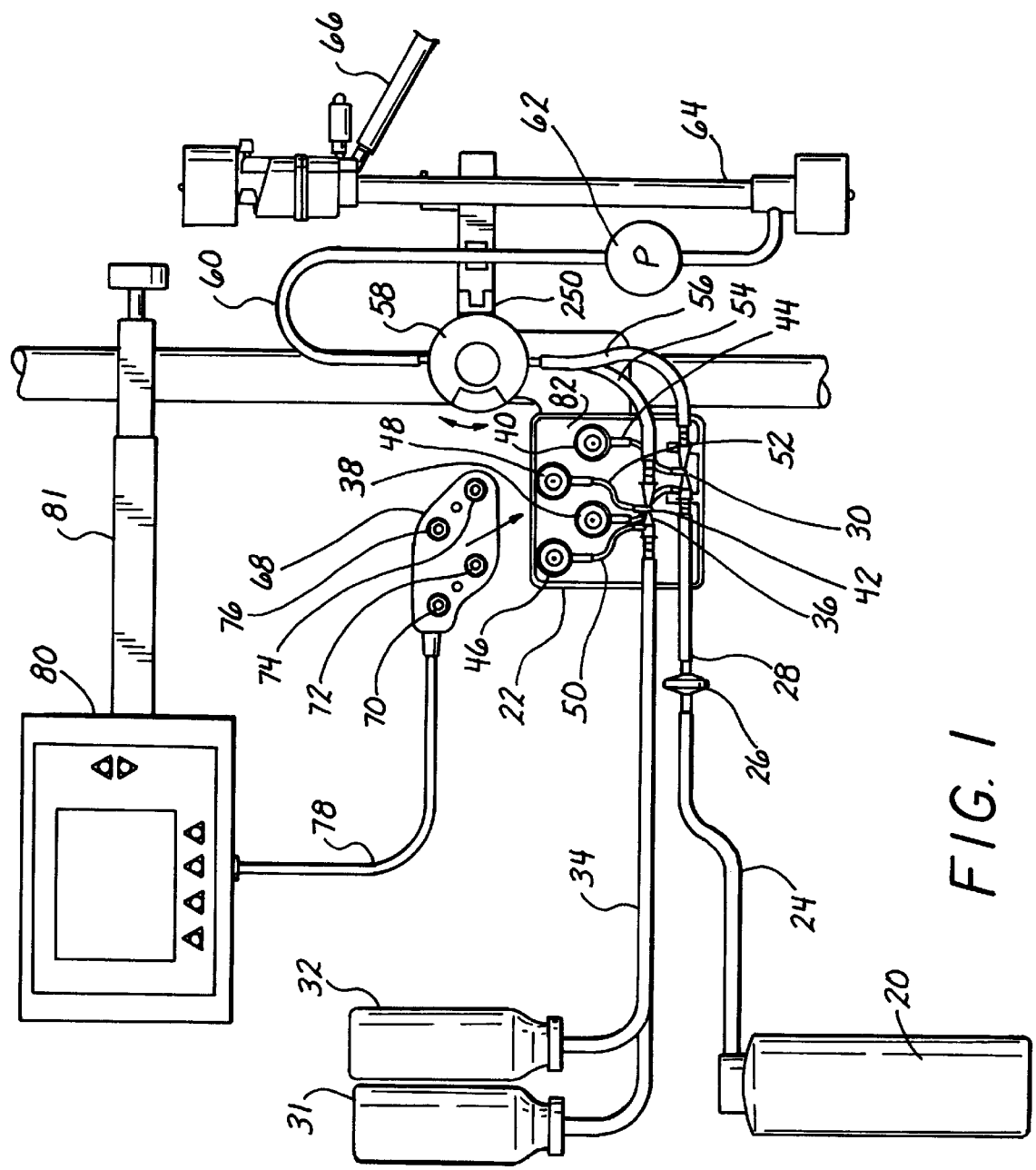
FIG. 1 shows a front view of the cardioplegia delivery monitoring system of the invention with portions broken away.
Figure 1A:
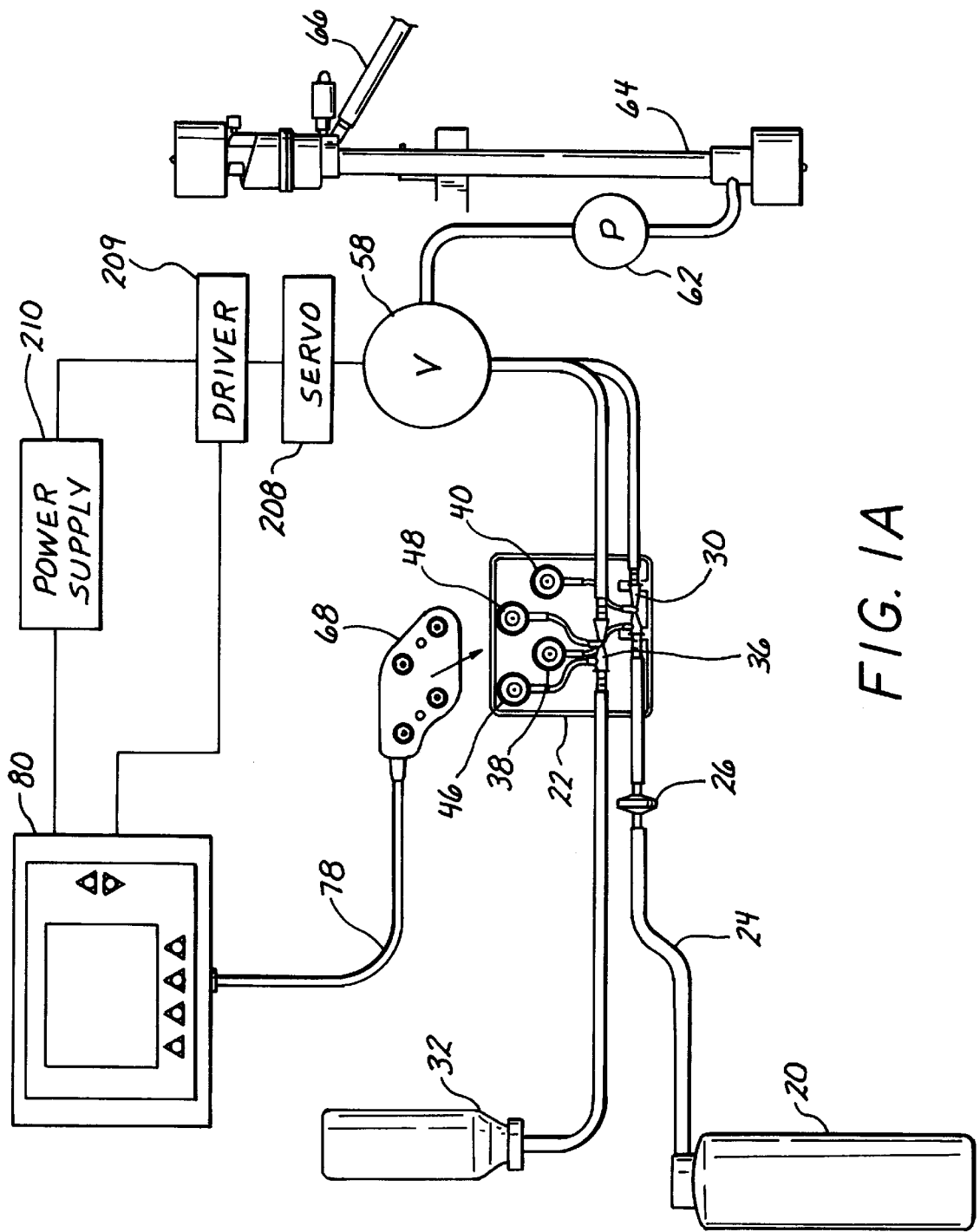
FIG. 1A shows a partially schematic front view of the cardioplegia delivery monitoring system of the invention.

Referring now to FIGS. 1 and 1A there can be seen an overall schematic showing of the cardioplegia system of the invention. As shown a source of blood 20 communicates with a venturi flow cell and transducer assembly or cassette 22 by means of a line or tubing 24 which passes through a one way check valve 26. The check valve 26 communicates with a line or tubing 28 which is connected to a venturi flow cell 30 for blood. The check valve 26 permits flow in one direction only and prevents oscillatory flow.

The venturi flow cell 30 which carries blood communicates with a transducer 38 and a transducer 40 by means of tubing or lines 42 and 44 respectively.

Two sources of crystalloid solution 31 and 32 selectively communicate with venturi flow cell and transducer assembly or cassette 22 by means of tubing or line 34 attached to a venturi flow cell 36.

The venturi flow cell 36 for crystalloid solution communicates with a transducer 46 and a transducer 48 by means of tubing or lines 50 and 52 respectively.

The transducers 38 and 40 detect pressure changes within venturi flow cell 30 and transducers 46 and 48 detect pressure changes within venturi flow cell 36.

The venturi flow cell 30 for blood communicates with variable ratio valve 58 by means of line or tubing 56. Similarly, venturi flow cell 36 for crystalloid solution communicates with variable ratio valve 58 by means of line or tubing 54.

The blood and/or crystalloid solution are combined within variable valve 58 and then exit the valve 58 by means of line or tubing 60. Line or tubing 60 passes through peristaltic pump 62 and heat exchanger 64. Tubing or line 66 exits heat exchanger 64 for delivery to a patient by means of tubing or line 66.

A transducer housing connector or hand set 68 contains quick connectors 70, 72, 74, and 76 which connect to transducers 46, 38, 48 and 40 respectively. The connectors 70, 72, 74, and 76 transmit signals from the transducers 46, 38, 48 and 40 respectively by means of line 78 to a microprocessor within monitor 80 held by support arm and holder 81.

The microprocessor converts the signals received from the transducers 46, 38, 48, and 40 into analogous electronic signals. Then, the microprocessor uses the electronic signals to calculate the flow rate through the venturi cells 30 and 36. The flow rate is then displayed on the monitor 80.

The method of the invention for delivery of cardioplegia includes the steps of providing at least one source of blood and providing at least one source of crystalloid solution.

The blood is flowed from at least one source of blood through a first passage having a convergent portion and a divergent portion separated by a constriction. The pressure within the convergent portion and within the constriction is then measured. The difference in measured pressure is calculated and then used to calculate the flow rate of the blood.

Similarly, the crystalloid solution is flowed from at least one source of crystalloid solution through a second passage having a convergent portion and a divergent portion separated by a constriction. The pressure within the convergent portion and within the constriction is then measured. The difference in measured pressure is calculated and then used to calculate the flow rate of the crystalloid solution.

The blood and crystalloid solution from the first and second passages are flowed into a chamber having means therein for selectively blocking all or a part of the flow from the first and second passages into the chamber.

Next the blood and/or the crystalloid solution is flowed from the chamber into a heat exchanger for temperature control of the blood and/or the crystalloid solution. Finally, the blood and/or crystalloid solution is delivered to a patient.

Preferably, the pressure difference is measured by passing the blood and the crystalloid solution into contact with one side of a diaphragm exposed to ambient pressure. The opposite side of the diaphragm is exposed to a conduit which is connected to an electronic device having means responsive to pressure to cause an electronic signal to be formed which is analogous to the pressure difference.

The electric signal is then sent to a microprocessor for calculating the pressure difference and flow rate of the blood and crystalloid solution. The calculated flow rates of the blood and crystalloid solution are displayed on a display monitor.

Looking more particularly at FIGS. 6–15A there can be seen the transducer and venturi flow cell assembly or cassette 22 in greater detail. As shown, the cassette 22 includes a top wall mounting plate or lid member 82 which is united along its peripheral edge to a bottom shallow box member 84. The top wall or lid member 82 is provided with openings 85, 86, 87, 88 for holding the transducers 46, 38, 48, and 40 respectively.

Similarly, the bottom or box member 84 is provided with openings 89, 90, 91, and 92 to hold the transducers 46, 38, 48, and 40 respectively.

Two additional pairs of slots or openings 93, 94 and 95, 96 in the top wall mounting plate or lid member 82 which are aligned with openings 93A, 94A and 95A, 96A in bottom or box member 84 to hold venturi flow cells 30 and 36.

Figure 10:
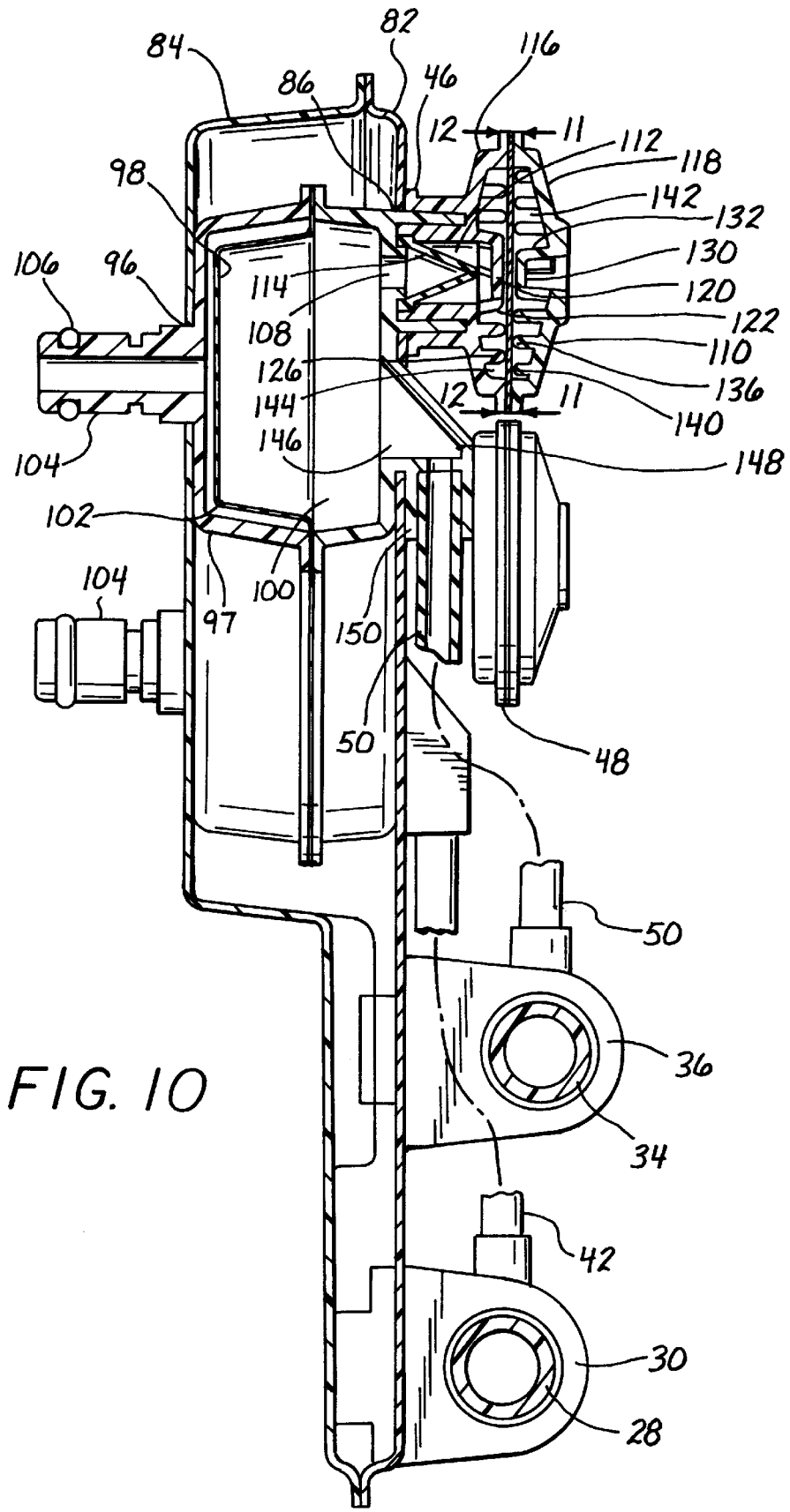
FIG. 10 shows a section through the transducer housing assembly taken along the lines 10—10 of FIG. 8.

An enlarged showing of the transducer 46 can be seen in FIG. 10. As shown, the transducer 46 includes a chamber or isolator 97 having a membrane or diaphragm 98 extending across the chamber 97. The membrane or diaphragm 98 divides or isolates the chamber 97 into an upper or first compartment 100 and a lower or second compartment 102. The membrane should be formed of a liquid impermeable material to prevent liquid from entering the lower compartment 102.

The lower compartment 102 includes a tubular projection 104 having an O-ring 106. The tubular projection 104 is adapted for snap connection to a connector 70 on transducer housing connector or hand set 68.

The upper compartment 100 has an opening or port 108 which communicates with a self-vent or autovent housing 110 through a passage or conduit 112 which contains a one way valve in the form of a duck bill valve 114.

Figure 11:
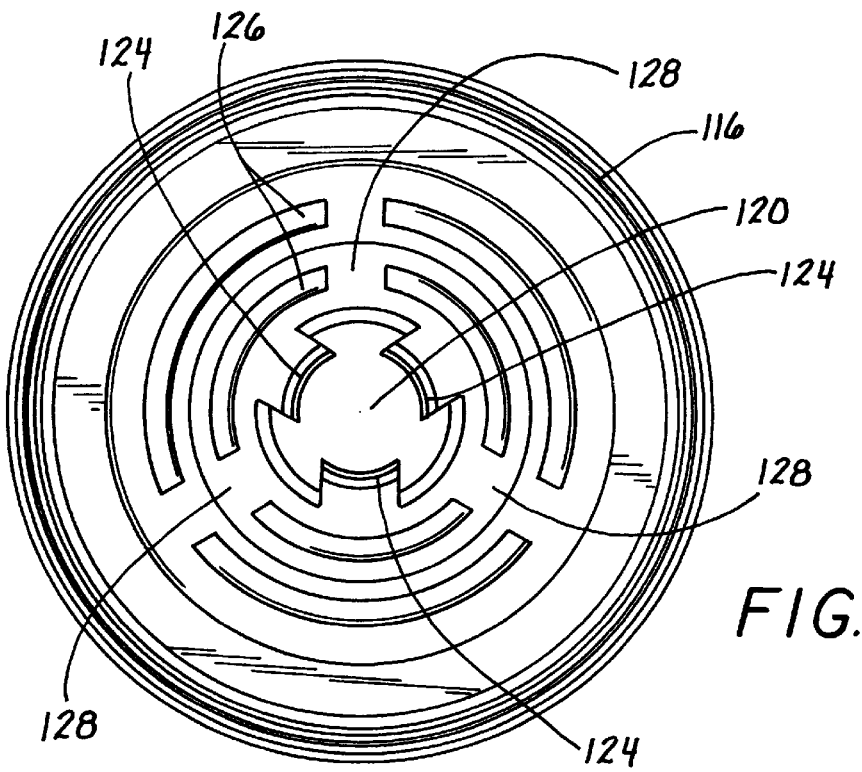
FIG. 11 shows a section through the autovent housing taken along the lines 11—11 of FIG. 10.
Figure 12:
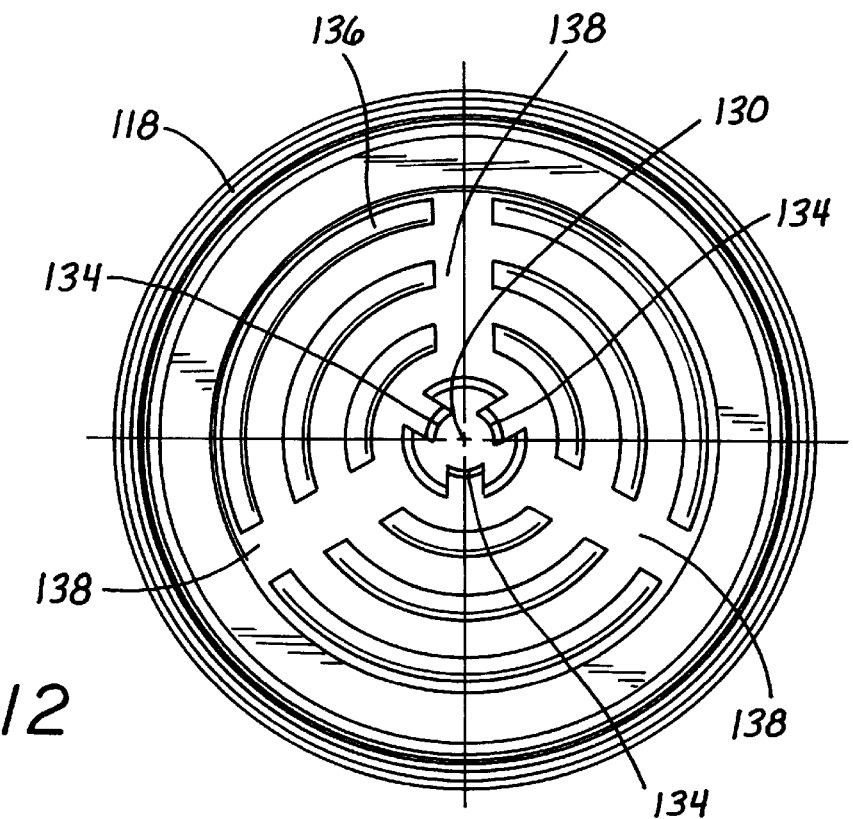
FIG. 12 shows a section through the autovent housing taken along the lines 12—12 of FIG. 10.

As seen more particularly in FIGS. 10, 11 and 12, the autovent housing or chamber 110 includes a generally concave base member 116 and a generally convex top member 118. The base member 116 has a central raised cap 120 having side walls 122 with openings 124 therein which communicate with passage or conduit 112 of upper compartment 100 of chamber 97. The raised cap 120 extends into the autovent housing or chamber 110.

A series of arc shaped curved ribs or ridges 126 on the interior surface of base member 116 form tiers surrounding the raised cap 120. The arc shaped ribs 126 are formed in increasing lengths as they are located distant from the raised cap 120. Between the tiers of curved ribs or ridges 126 are areas free of ribs or ridges 126 adapted to form ramps or passages 128 between the tiers of ridges 126.

In a similar fashion as seen particularly in FIG. 12, the top member 118 includes a depressed cup member or covering 130 having side walls 132 with openings 134 therein. The cup member 130 extends into the autovent or self-vent housing 110.

A series of arc shaped curved ribs or ridges 136 on the interior surface of top member 118 form tiers surrounding the cup member 130. The arc shaped ribs 136 are formed in increasing lengths as they are located distant from the cup member 130. Between the tiers of curved ribs or ridges 136 are areas free of ribs or ridges 136 adapted to form channels or passages 138 between the tiers of ridges 136.

As shown in FIG. 10, between the base member 116 and the top member 118 is disposed a membrane 140. The membrane 140 divides the autovent housing 110 into an upper chamber or cavity 142 and a lower chamber or cavity 144. The membrane 140 is of the type which will permit the passage of air or other gas but not liquid. A preferred membrane is a 0.45 micron filter membrane formed of polytetrafluoroethylene (PTFE). Other membrane materials can be used as long as the membrane will pass air or other gas but not liquids.

The presence of the ribs 126 and 136 prevents the possibility of the membrane 140 from sealing to the top member 118 or the base or lower member 116. The cup shaped member 130 protects the membrane from accidental damage. The dome shape of the top member 118 together with the channels or passages 138 aid the exit of air or other gas from the autovent housing 110.

The upper compartment 100 of the chamber or isolator 97 has a port 146 which extends upwardly into a raised tubular member 148 having an extension 150 for receipt of a small diameter tube 50. The tube 50 is connected to venturi flow cell 36 for crystalloid solution.

Preferably, the transducers 38, 40, 46, and 48 are made of a clear plastic material such as polycarbonate or polyvinyl chloride. Use of a clear plastic material permits the visual inspection of the transducers to determine if the blood or crystalloid solution is flowing properly.

Figure 14A:
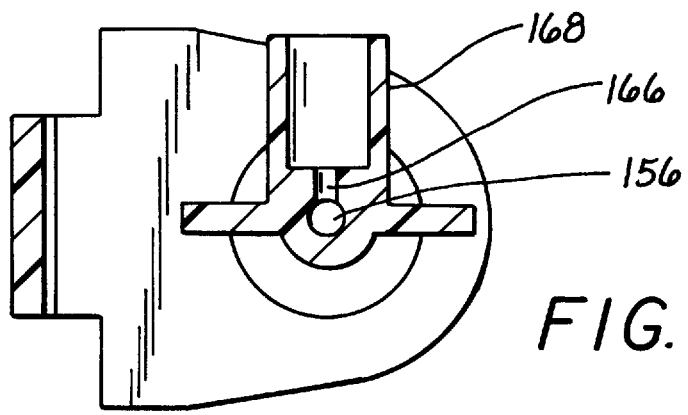
FIG. 14A shows a cross section of the venturi flow cell for blood of FIG. 13 taken along the lines 14A—14A of FIG. 14.

A detailed view of the venturi flow cell 30 which carries blood can be seen in FIGS. 13, 14, and 14A. The venturi flow cell 36 which carries crystalloid solution has different dimensions from venturi flow cell 30 as hereinafter described. However, the venturi flow cell 36 operates in the same manner as venturi flow cell 30. The differences in dimensions are related to the different fluids of crystalloid solution and blood. These dimensions compensate for the differences in viscosity over a range of flow rates and over a range of temperatures.

As shown, venturi flow cell 30 for blood is formed of a relatively short tube 154 having a constricted, narrowed portion or throat 156. The upstream inlet side or converging portion 158 of the constriction or throat 156 is formed into a barbed end 160 for connection to tube 28. A relatively narrow diameter pressure port or tap 162 in the upstream inlet or converging side or portion 158 of venturi flow cell 30 opens into a relatively large diameter tubular extension or conduit 164 for connection to conduit or tube 42 to transducer 38.

Directly above the constricted portion or throat 156 is a small diameter pressure port or tap 166 which opens into a relatively large diameter tubular extension or conduit 168 for connection to conduit or tube 44 to transducer 40.

The downstream outlet or diverging side 170 of venturi flow cell 30 for blood is also formed into a barbed end 172 for slip fit connection to tube or conduit 56.

The upstream inlet or converging side 158 of the venturi flow cell 30 for blood decreases in diameter from pressure port or tap 162 to the constriction or throat 156. On the downstream outlet or diverging side 170 of the throat 156, the venturi flow cell 30 increases in diameter. The upstream inlet or converging side 158 and the downstream outlet or diverging side 170 of the venturi flow cell 30 are not symmetrical.

Figure 15A:
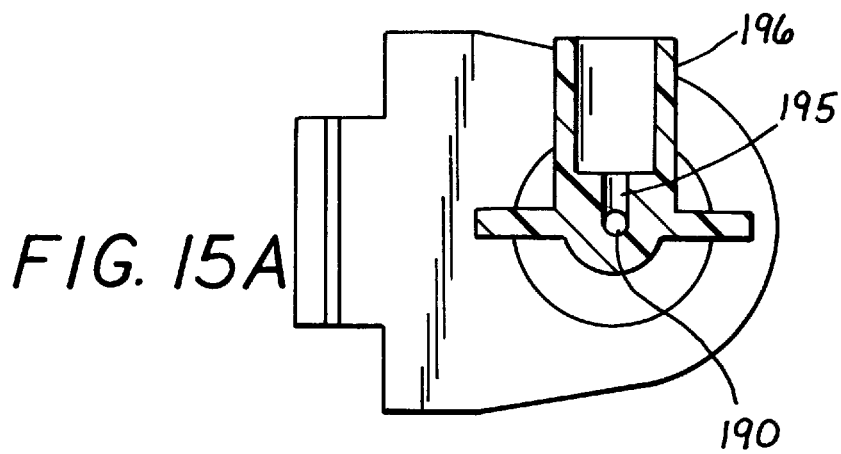
FIG. 15A shows a cross section taken along the lines 15A—15A of FIG. 15.
Figure 15:
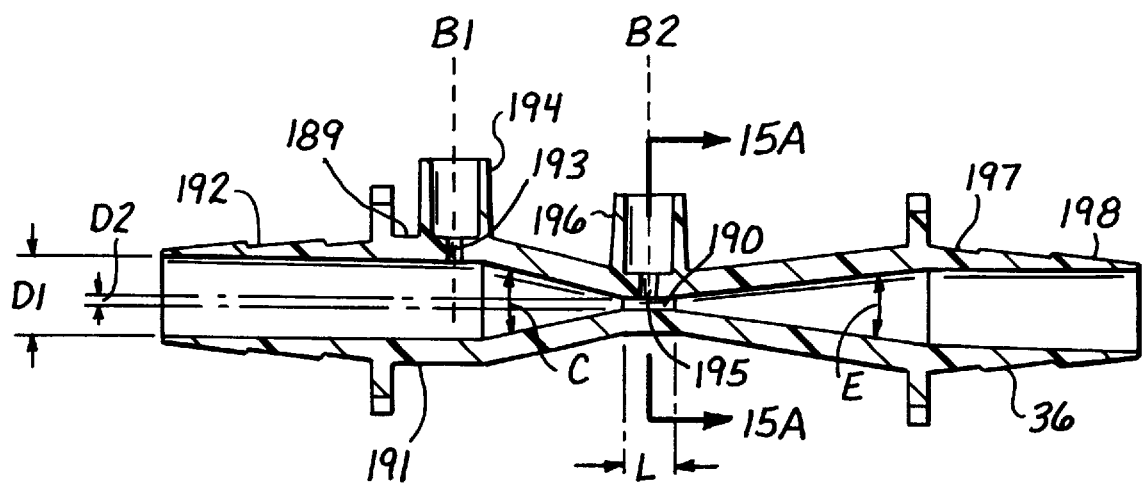
FIG. 15 shows an axial section of the venturi flow cell for crystalloid solution taken along the lines 15—15 of FIG. 8.

A detailed view of the venturi flow cell 36 which carries crystalloid solution can be seen in FIGS. 15 and 15A. As shown, venturi flow cell 36 for crystalloid solution is formed of a relatively short tube 189 having a constricted, narrowed portion or throat 190. The upstream inlet or converging side or portion 191 of the constricted portion or throat 190 is formed into a barbed end 192 for connection to tube 34.

A relatively narrow diameter pressure port or tap 193 in the upstream inlet or converging side or portion 191 of venturi flow cell 36 opens into a relatively large diameter tubular extension or conduit 194 for connection to conduit or tube 50 to transducer 46.

Directly above the constricted portion or throat 190 is a small diameter pressure port or tap 195 which opens into a relatively large diameter tubular extension or conduit 196 for connection to conduit or tube 52 to transducer 48.

The downstream outlet or diverging side 197 of venturi flow cell 36 for crystalloid is also formed into a barbed end 198 for slip fit connection to tube or conduit 54. The upstream inlet or converging side 191 of the venturi flow cell 36 for crystalloid decreases in diameter from pressure port 193 to the throat 190. On the downstream outlet or diverging side 197 of the throat 190, the venturi flow cell 36 increases in diameter. The upstream inlet or converging side 191 and the downstream outlet or diverging side 197 of the venturi flow cell 36 are not symmetrical.

It is important to note that the venturi flow cell 30 for blood and the venturi flow cell 36 for crystalloid have different dimensions. In particular, as seen in FIGS. 13, 14, 14A, 15, and 15A, the diameter of the throat or constricted portion 156 of venturi flow cell 30 for blood is larger and longer in length than the throat or constricted portion 190 of venturi flow cell 36 for crystalloid solution.

For example, the venturi flow cell 30 for blood preferably has an upstream inlet or convergent portion interior diameter, D1, in the range of 6.0–7.0 mm, and most preferably in the range of about 6.5 mm±0.05 mm.

The cross sectional area, A1, of the upstream inlet or convergent portion is preferably in the range of 25 mm² to 34 mm², and most preferably is about 29 mm².

The diameter, D2, of the constriction or throat 156 is preferably in the range of 1.6–2.0 mm, and most preferably has a diameter of about 1.8±0.05 mm.

The cross sectional area, A2, of the constriction or throat 156 is at least 2 mm². Preferably, the cross sectional area, A2 is in the range of 2 mm² to 3 mm², and most preferably is about 2.5 mm².

The ratio of the cross sectional area, A1 of the convergent portion and the cross sectional area, A2, of the constriction or throat is preferably in the range of about 8.33 to 1 to about 17 to 1. Most preferably the ratio is 11.6 to 1.

The length, L, of the constriction or throat 156 is preferably in the range of 8.0–9.0 mm, and most preferably in the range of 8.5 mm±0.05 mm.

The pressure ports or taps 162 and 166 have axial centers, B1 and B2, which are preferably in the range of 10.0–20.0 mm apart and most preferably are 15 mm±0.3 mm apart.

For best results, the convergent cone angle, C, of the venturi flow cell 30 for blood is in the range of 20°–30° and most preferably is 26°±1°.

The divergent cone angle, E, of the venturi flow cell 30 for blood is preferably in the range of 10°–20°, and most preferably is in the range of 15°±1°.

For the venturi flow cell 36 for crystalloid solution, the upstream or inlet interior diameter, D1, is preferably in the range of 5.6–6.6 mm, and most preferably 6.1 mm±0.05 mm.

The cross sectional area, A1, of the upstream inlet or convergent portion is preferably in the range of 25 mm² to 34 mm², and most preferably is about 29 mm².

The diameter, D2, for the constriction or throat 190 is preferably in the range of 0.8–1.2 mm and most preferably is in the range of 1 mm±0.05 mm.

The cross sectional area, A2, of the constriction or throat 156 is at least 0.5 mm². Preferably, the cross sectional area, A2 is in the range of about 0.5 mm² to about 1.13 mm², and most preferably is about 0.78 mm².

The length, L, of the constriction or throat 190 is preferably in the range of 3.5–4.5 mm, and most preferably is in the range of 4 mm±0.13 mm.

The ratio of the cross sectional area, A1, of the upstream inlet or convergent portion to the cross sectional area, A2, of the constriction preferably is in the range of about 22 to 1 to about 68 to 1. Most preferably, the ratio is 37.1 to 1.

The pressure ports or taps 193 and 195 have axial centers, B1 and B2, which are preferably in the range of 10.0–20.0 mm apart, and most preferably are in the range of 15 mm±0.3 mm apart.

For best results, the convergent cone angle, C, of the venturi flow cell 36 for crystalloid solution is preferably in the range of 20°–30°, and most preferably in the range of 26°±1°.

The divergent cone angle, E, of the venturi flow cell 36 for crystalloid solution is preferably 10°–20°, and most preferably is in the range of 15°±1°.

It is important that the location and distance between the pressure port or tap 162 and pressure port or tap 166, and the location and distance between the pressure port or tap 193 and the pressure port or tap 195, and the volume be fixed and known in order to be able to calculate the flow rate through each venturi cell 30 and 36 by means of the pressure drop between pressure ports. With the flow rate known, the quantity of fluid flowing can be calculated.

The Venturi Principle equation to be used to calculate the quantity of fluid flowing through the venturi flow cells 30 and 36 is given below:

$$Q = \frac{CvA1A2}{\sqrt{A1^2 - A2^2}} \times \sqrt{\frac{2 \times \Delta P}{D}}$$

wherein:
$A1 = D1^2 \pi/4$
$A2 = D2^2 \pi/4$
$\Delta P = P1 - P2$

A1 is the cross sectional area at the pressure port or tap opening into the upstream or convergent side of the venturi cell.

A2 is the cross sectional area at the pressure port or tap opening into the throat or constricted portion.

D is the density of the fluid going through the flow cell.

D1 is the upstream or inlet interior diameter of the venturi flow cell.

D2 is the diameter of the throat or constricted area.

$C_v$ is the velocity coefficient which is determined by the identity of the fluid and the Reynolds number and is unique to the geometry of the venturi flow cell.

P1 is the pressure at the pressure port or tap opening into the upstream or convergent side of the venturi cell.

P2 is the pressure at the pressure port or tap opening into the throat or constricted portion.

Q is the flow rate.

In order to calculate the $C_v$, empirical tests are conducted using for example, blood flow within the venturi flow cell for blood within a wide range of known flow rates. Then, the results obtained using the venturi cells are compared with the known flow rates. The differences between the two values constitute the $C_v$. The different $C_v$ values are then plotted so that the appropriate correction for each flow rate can be used to provide an accurate result. Thus, a correction factor is determined for each flow rate for a given fluid through a specific venturi flow cell. The correction factor together with the Venturi Equation is incorporated into the software used in the microprocessor within the monitor 80 so that a corrected value is displayed on the monitor.

Figure 26:
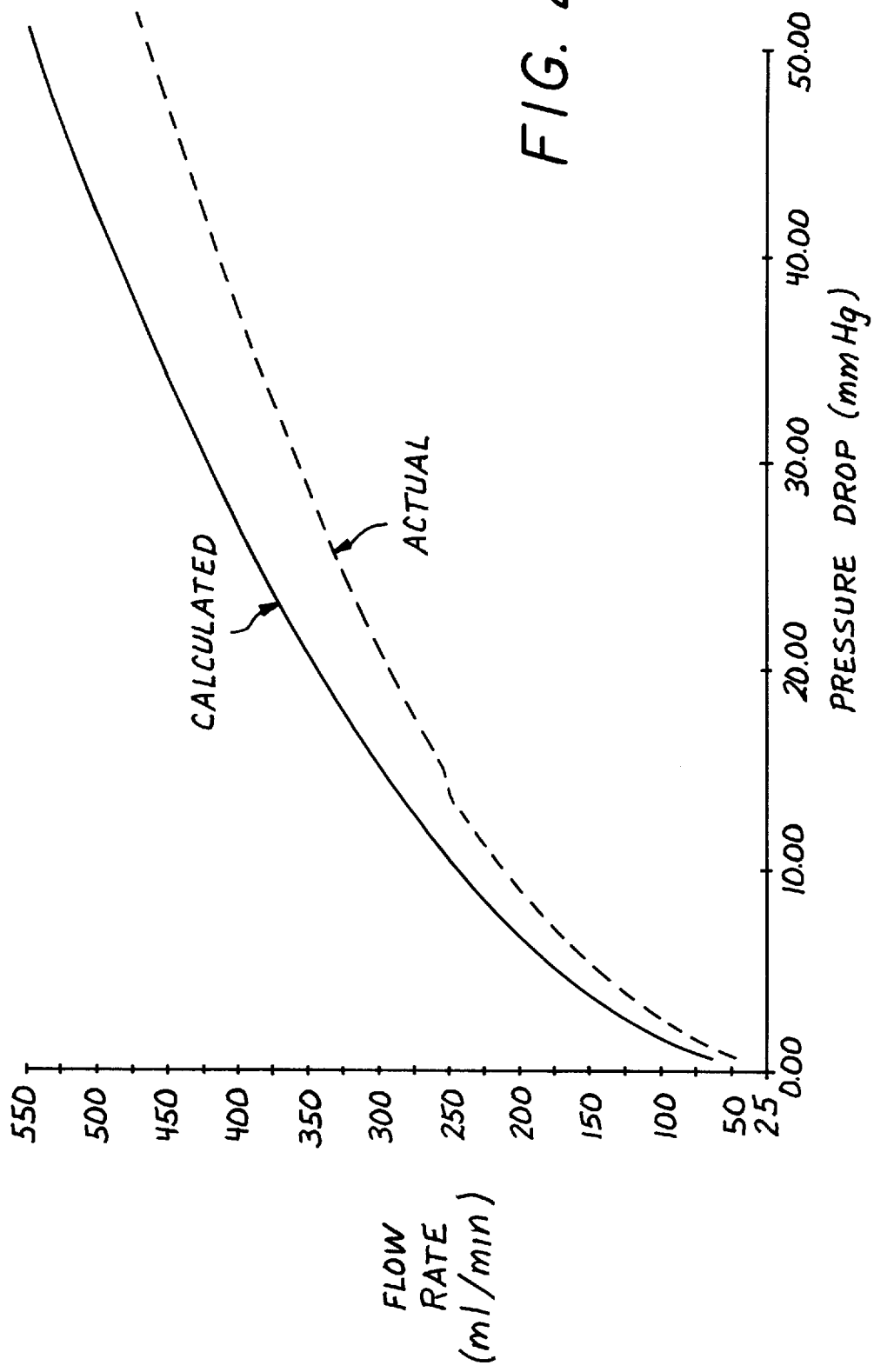
FIG. 26 shows a graph comparing the real and calculated flow rate through a venturi flow cell for blood.

An example of a graph of blood flow over a wide range of known flow rates for a given venturi flow cell for blood is shown in FIG. 26.

The specific dimensions of the venturi flow cells have been found to avoid turbulence which could give a false pressure reading.

The venturi flow cells 30 and 36 are supported by a pair of side brackets or struts 174 and 176 which surround the upstream inlet end 158 and the downstream outlet end 170 respectively. Between the brackets or struts 174 and 176 are a pair of reinforcing ribs or fins 178 and 180.

As shown particularly in FIG. 13, the bracket 174 has an extension 182 which terminates in a detent or catch 184. The other bracket 176 also extends away from the cell 30 to form a right angle extension 186 which has a flange or lip 188 at the end. The flange or lip 188 is retained by the detent or catch 184 on the bracket 174.

The mounting plate or top member 82 of the cassette 22 contains two pairs of slots or openings 93, 94 and 95, 96 which receive the brackets 174 and 176 of the venturi flow cells 30 and 36.

The brackets 174 and 176 of the venturi flow cells 30 and 36 are secured under the mounting plate or top member 82 by means of the flange or lip 188 on extension 186 engaging the detent or catch 184 on the bracket 174.

Figure 2:
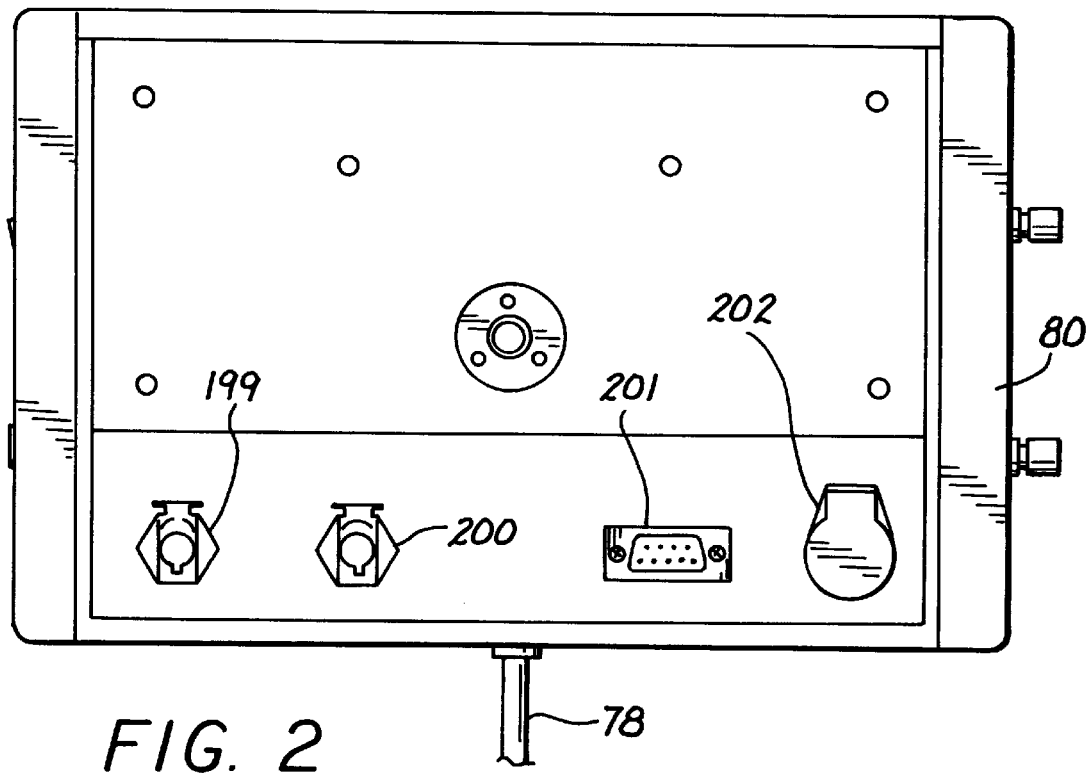
FIG. 2 shows a rear view of the monitor of FIGS. 1 and 1A.

The microprocessor based VCR monitor 80 receives data in the form of process signals to derive blood and crystalline flow and volume, and to measure antegrade and retrograde pressure and solution temperature. As shown in FIGS. 2–5, the monitor 80 receives data from the cassette 22 through the line 78. Other connectors for receipt of data can be found at the rear of the monitor 80 as shown in FIG. 2.

The antegrade infusion pressure data or information is received through port or connector 199. The retrograde infusion pressure data is received through port or connector 200. Downloading of data to a computer or to a printer can be done through connector 201. The data from a temperature probe is received through connector 202.

Figure 3:
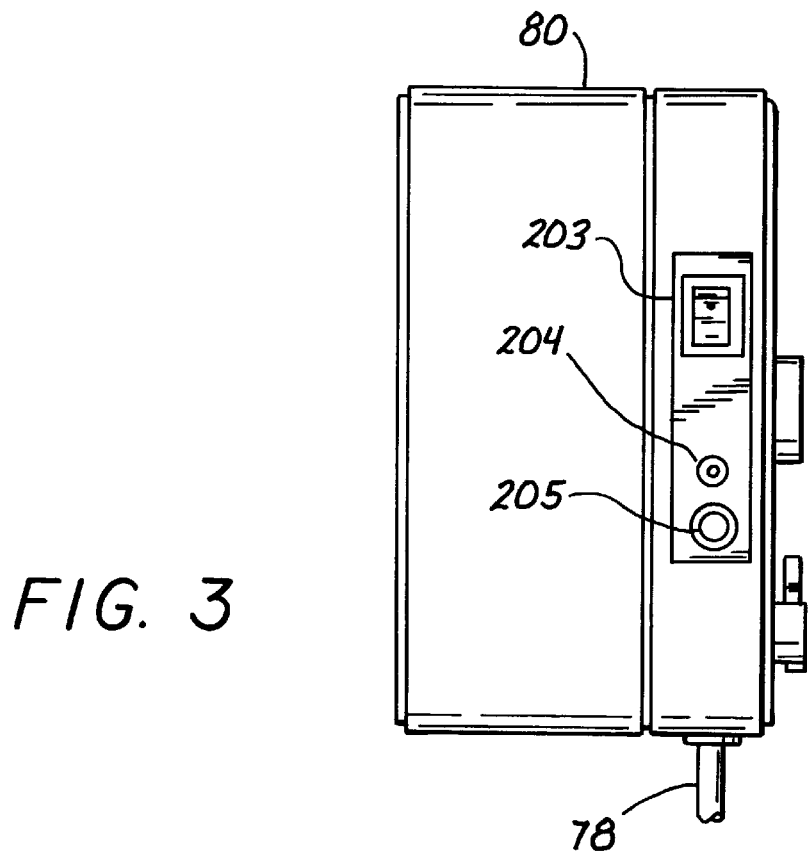
FIG. 3 shows a side view of the monitor of FIG. 2.
Figure 4:
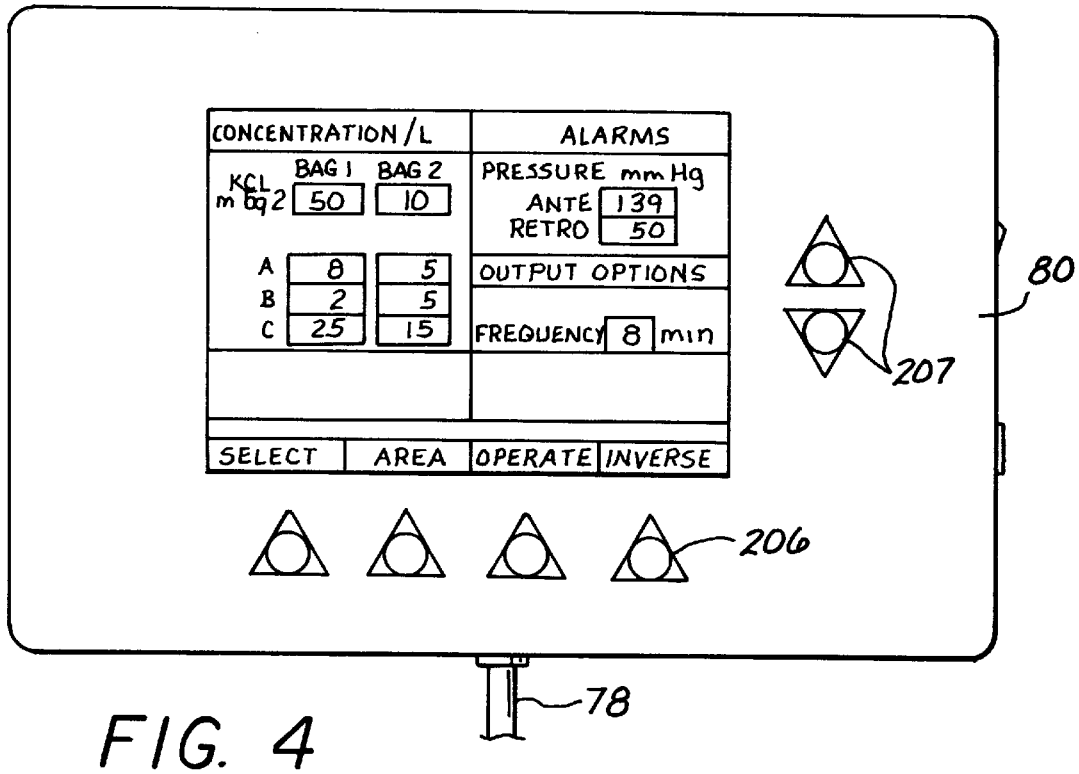
FIG. 4 shows a view of one screen display for the monitor of FIG. 2.
Figure 5:
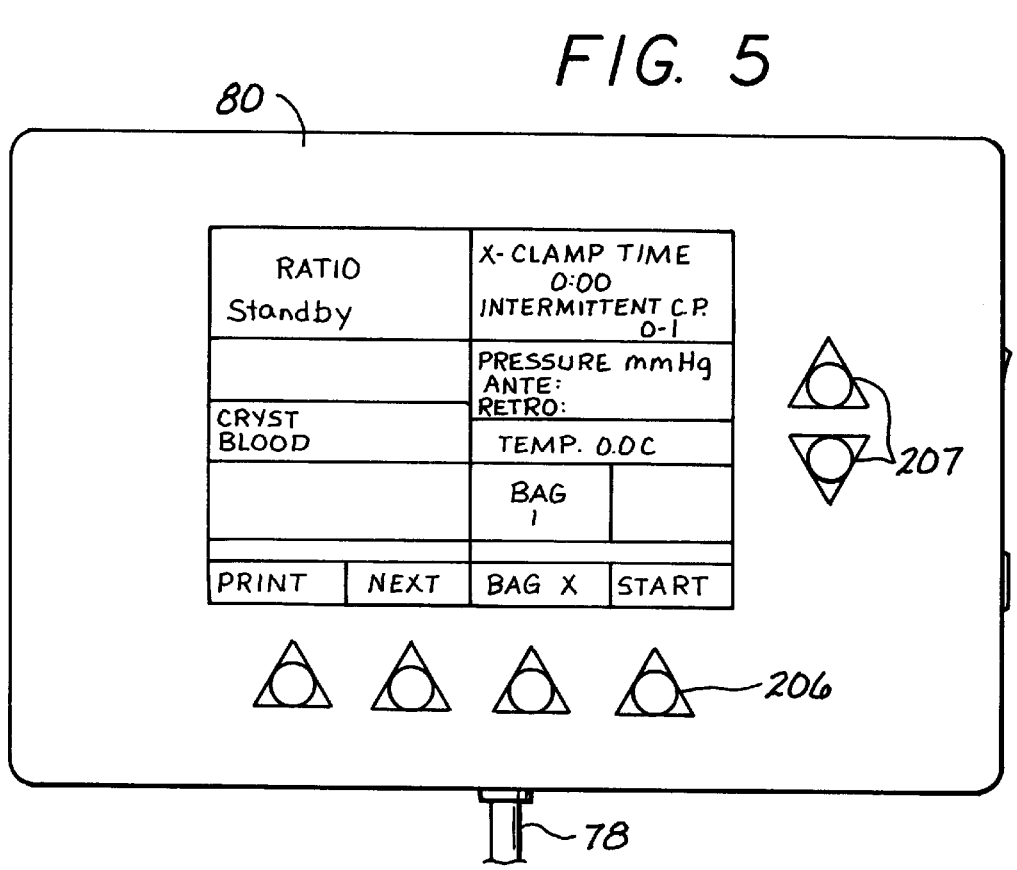
FIG. 5 shows a view of another screen display for the monitor of FIG. 2.
Figure 7:
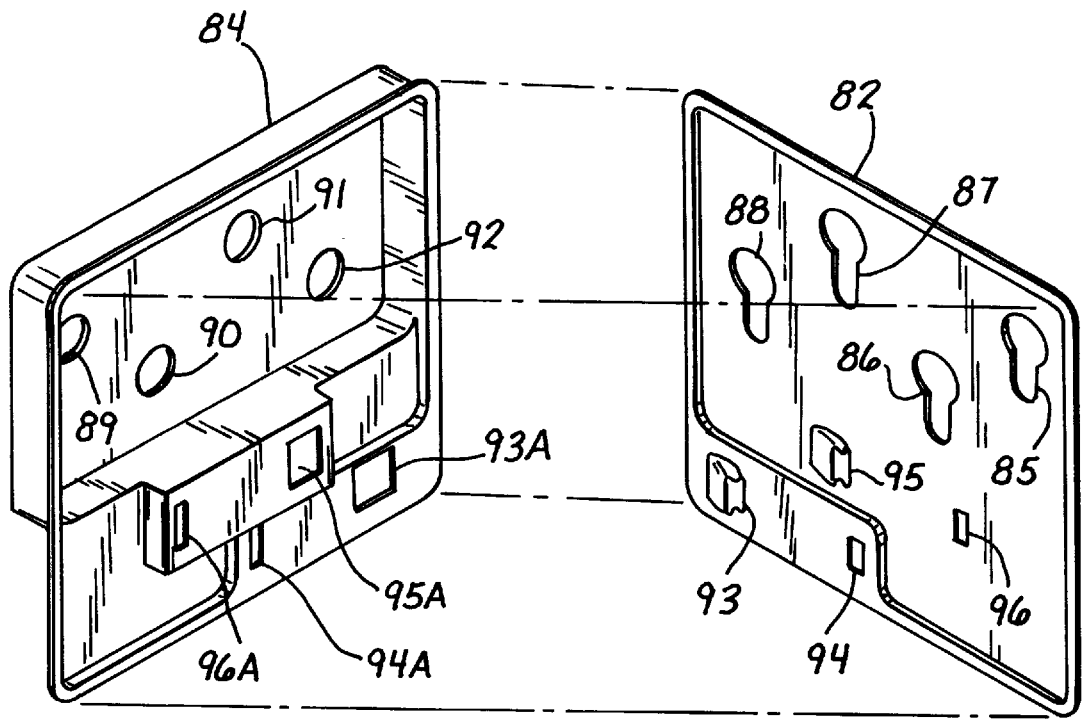
FIG. 7 shows a perspective view of the top and bottom members of the transducer and venturi flow cell housing in the open condition.
Figure 6:
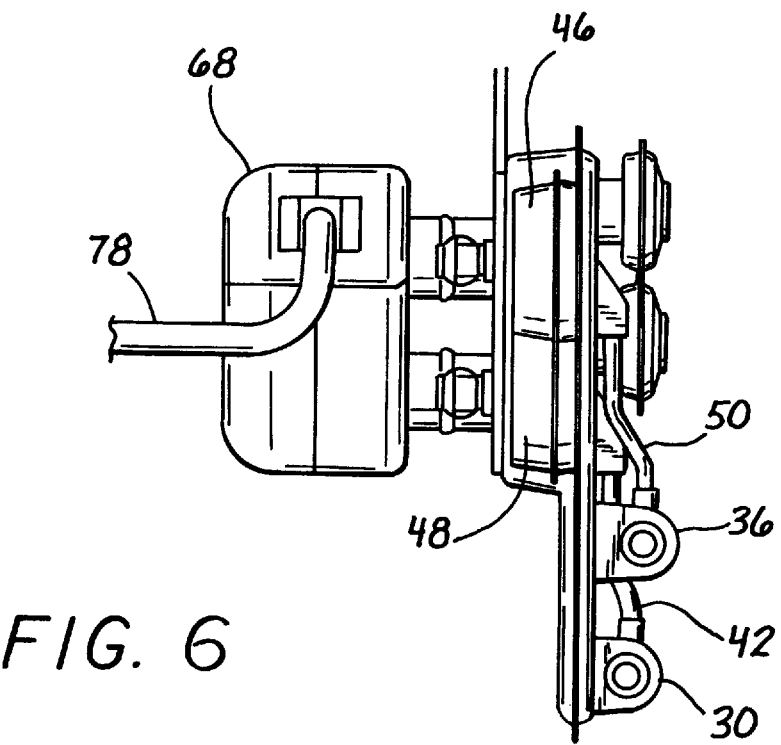
FIG. 6 shows a side view of the transducer and venturi flow cell housing assembly.
Figure 9:
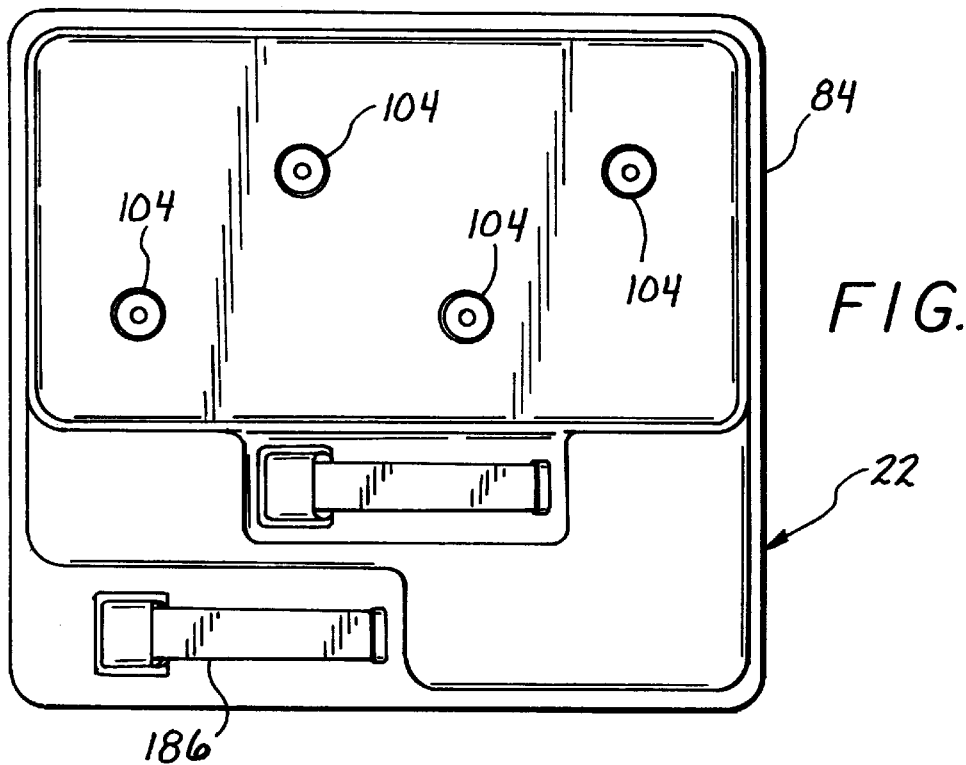
FIG. 9 shows a bottom plan view of the transducer and venturi flow cell housing assembly.
Figure 8:
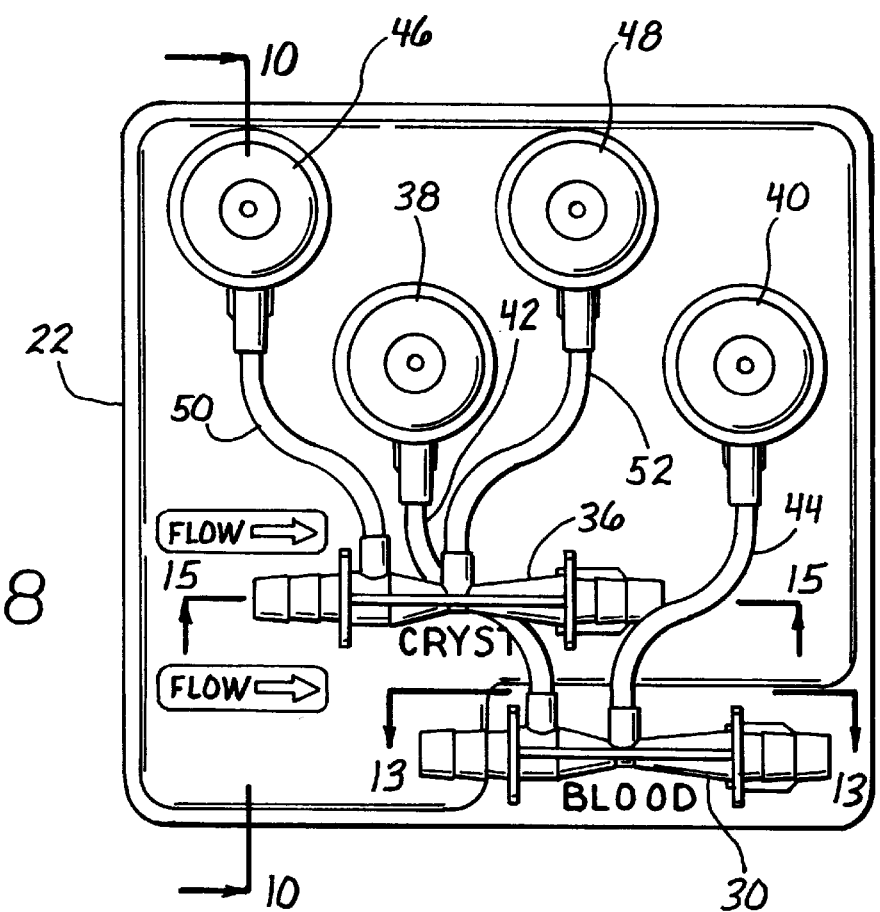
FIG. 8 shows a top plan view of the transducer and venturi flow cell housing assembly.

FIG. 3 shows a side mounted power switch 203, a charging indicator 204, and a port 205 for an A/C adaptor. The port 205 connects to a 12 Volt, Nickel-Metal Hydride rechargeable Battery Pack within the monitor 80. FIGS. 4 and 5 show two different screen displays for display of information received through the ports 199, 200, 201, 202, and through line 78 from cassette 22. Entering information and switching between functional screens of the monitor 80 is made through menu switches 206 and up/down rocker switches 207.

While the flow rate is displayed on the monitor 80, the relative ratio of blood and crystalloid solution is determined by the operation of a variable ratio valve 58.

The variable ratio valve 58 is unique in that it can be manually operated to provide all crystalloid solution, all blood, or any ratio of crystalloid solution and blood.

As an alternative to manual operation, as indicated in FIG. 1 A, the valve 58 can be operated by a servo 208 which responds to electrical impulses from a driver 209 which receives commands from the microprocessor within the microprocessor based VCR monitor 80.

With respect to the manual operation, as shown particularly in FIGS. 16–21, the variable ratio valve 58 includes a valve housing 211. The valve housing 211 includes a cylindrical chamber 212 having an opening 214 in the base of the chamber 212.

The top of the chamber 212 is open and is surrounded by an outer circular flange 216. The flange 216 has two detents or raised stops 218 and 220 shown in outline in FIG. 21 on its top surface.

As shown in FIG. 17, a pair of inlet ports 222 and 224 communicate with two parallel tubular projections 226 and 227 respectively. The tubular projections 226 and 227 extend from the valve housing 211. Each tubular projection 226 and 227 has an inner chamber 228 and 229 having a one way check valve disposed therein in the form of a duck bill valve 230 and 232 respectively.

In order to facilitate connection with tubing 54 and 56 from the venturi flow cells 36 and 30, the tubular projections 226 and 227 are provided with barbed tapered ends 234 and 236 respectively. In this manner, crystalloid solution from venturi flow cell 36 flows through tubing 54 to barbed end 234 into tubular projection 226 through duck bill valve 230 in chamber 228 to enter chamber 212 of variable ratio valve 58.

Similarly, blood from venturi flow cell 30 flows through tubing 56 to barbed end 236 into tubular projection 227 through duck bill valve 232 in chamber 229 to enter inlet port 224 of chamber 212 in variable ratio valve 58.

Opposite the inlet ports 222 and 224 is an outlet port 238 having a tubular projection 240 extending therefrom. The tubular projection 240 extends from the valve housing 211 and has a barbed tapered end 242 to facilitate connection to tubing 60.

The axial centers of inlet ports 222 and 224 and the outlet port 238 lie in a plane which bisects the axial center 244 of chamber 212.

Tubular projections 226 and 227 are supported by a bracket or strut 244. Similarly, a bracket or strut 246 supports tubular projection 240.

Another pair of brackets or struts 247 and 248 are disposed on opposite sides of the valve housing 211 to serve as a means for securing the variable ratio valve 58 to a holder 250.

A substantially cylindrical cup shaped valve core member 252 is mounted for rotation within the chamber 212. The valve core member 252 has a bottom tubular projection 254 which is sized to fit into opening 214 in the bottom of chamber 212. The tubular projection 254 can be secured within opening 214 by means of a C-clip 256.

Surrounding the exterior of the cylindrical valve core member 252 are two spaced apart substantially parallel raised rings, bands or cams 258 and 260. Within chamber 212, band or cam 258 overlies inlet port 222 for crystalloid solution and band or cam 260 overlies inlet port 224 for blood. The width of band or cam 258 and band or cam 260 is great enough to cover inlet ports 222 and 224 respectively. This can be seen in FIGS. 17 and 20.

The circular space between each band, ring, or cam 258 and 260 forms a channel or passage 262. Channel or passage 262 is in fluid communication with outlet port 238.

Each band 258 and 260 is eccentric. Thus, as valve core 252 is rotated over a prescribed arc of travel within valve housing 211, the gap or space overlying channel 222 increases while the gap or space overlying channel 224 decreases or vise versa, depending of the direction of rotation. The bands 258 and 260 are arranged so that the deepest or thickest point of band 258 is adjacent to the thinnest point of band 260.

Figure 18:
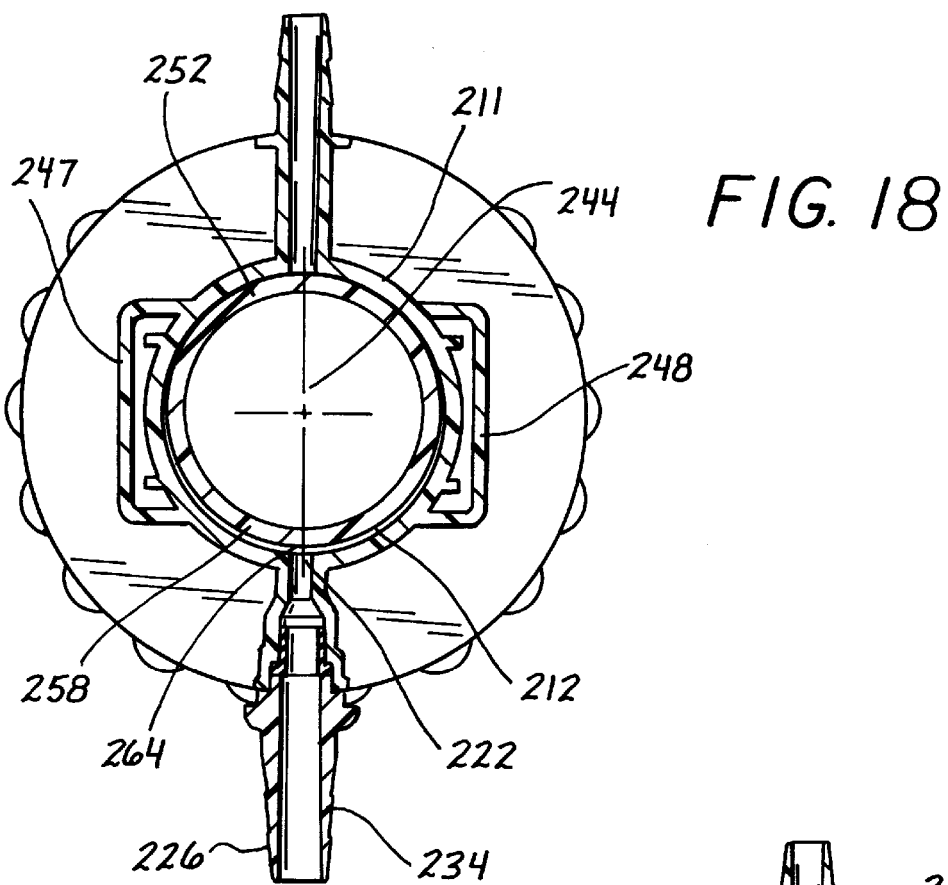
FIG. 18 shows a section through the valve of FIG. 16 taken along the lines 18—18 of FIG. 17.
Figure 19:
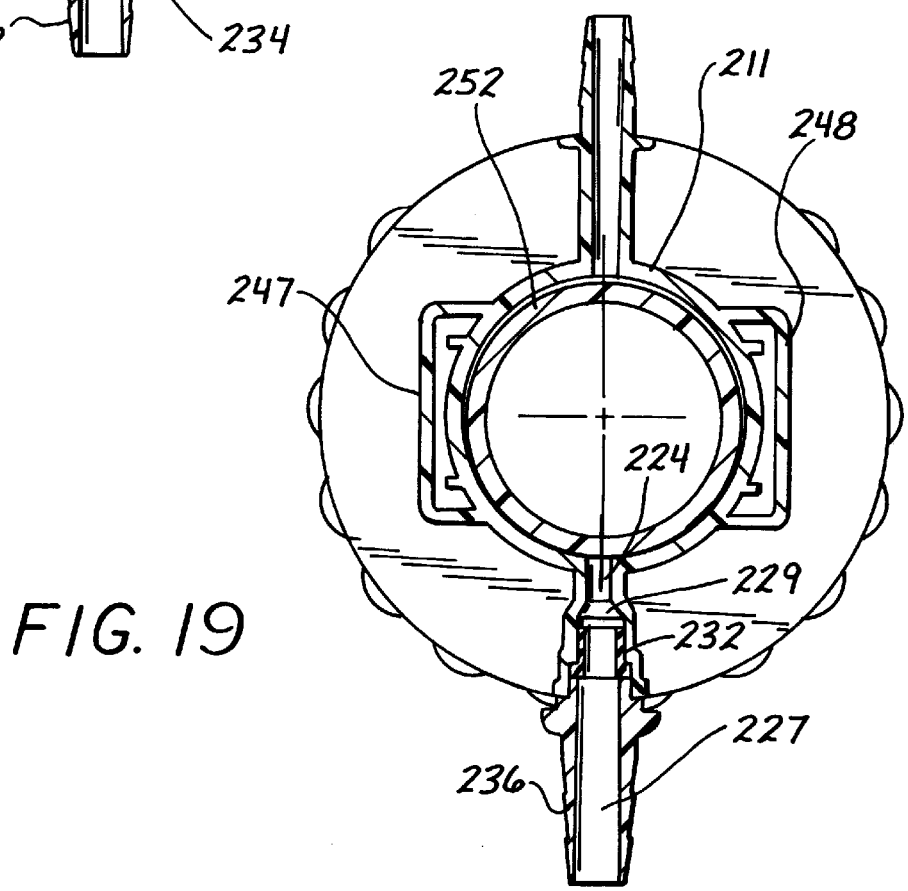
FIG. 19 shows a section through the valve of FIG. 16 taken along the lines 19—19 of FIG. 17.
Figure 20:
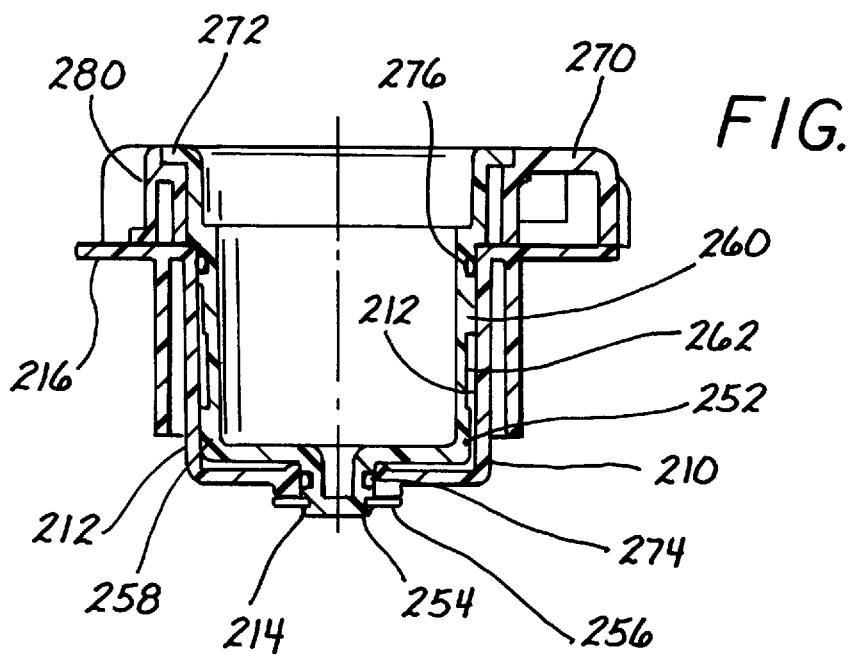
FIG. 20 shows a cross section taken along the lines 20—20 of the valve of FIG. 16.

In this manner, as shown in FIGS. 17, 18 and 19, when band 258 has its thinnest portion overlying inlet port 222 there is a space 264 between the band 258 and the inlet port 222. As shown in FIG. 17, this permits crystalloid solution to enter port 222 as indicated by the arrows. From inlet port 222, the crystalloid solution enters channel 262 where it enters outlet port 238.

At the same time, as seen in FIG. 19, band 260 has its thickest portion overlying inlet port 224 so that entry of blood is effectively blocked.

The above condition is effected when the inner valve core member 252 is rotated counterclockwise until it is stopped by detent 218. Rotation of the inner cup shaped valve core member 252 clockwise until it is stopped by detent 220 brings about the opposite effect. That is, band 258 has its thickest portion overlying inlet port 222 blocking entry of crystalloid solution. Concurrently, band 260 has its thinnest portion overlying inlet port 224 so that blood can enter into chamber 212, through channel 262 to outlet port 238.

The increasing and decreasing thickness of bands or cams 258 and 260 provides a gradually increasing and decreasing ramp function along the path of rotation. The bands do not have to be mirror images of each other. Thus, the increasing and decreasing ramp function does not have to be even but can be adjusted specifically for the density of the fluid, i.e. blood, or crystalloid solution.

In this manner, rotation of the valve core member 252 over a prescribed arc of travel permits the ratio of crystalloid to blood to be infinitely varied from all crystalloid, mixtures of blood and crystalloid in all proportions, to all blood depending on the degree of rotation.

Channel 262 is always open to outlet port 238 regardless of the position of bands 258 and 260.

Surrounding the cup shaped valve core member 252 is a rotatable collar 270 which is disposed between the valve housing 211 and an upper flange 272 surrounding the top of valve core member 252. With the bottom 254 of core member 252 secured within opening 214 in chamber 212, the collar 270 is held in place.

An O-ring 274 surrounds and seals the bottom tubular projection 254 within opening 214 of chamber 212. Another O-ring 276 seals the upper portion of core member 252 within chamber 212. This can be seen in FIGS. 17 and 20.

A graphical scale 278 showing rotation position over a prescribed arc of travel is disposed about the circumference of the outer flange 216 of chamber 212. This scale 278 can be substituted with any equivalent scale or divisions to indicate the relative proportions of blood and crystalloid solution admitted to channel 262 in chamber 212.

The collar 270 includes an opening or window 280 which reveals the scale 278. A pointer or arrow 282 marks the divisions on the scale 278. Sidewall 284 of the window 280 is stopped by detent 218 when the collar 270 and valve core member 252 are rotated clockwise. Sidewall 286 of the window 280 is stopped by detent 218 when the collar 270 and core member 252 are rotated counterclockwise.

Figure 21:
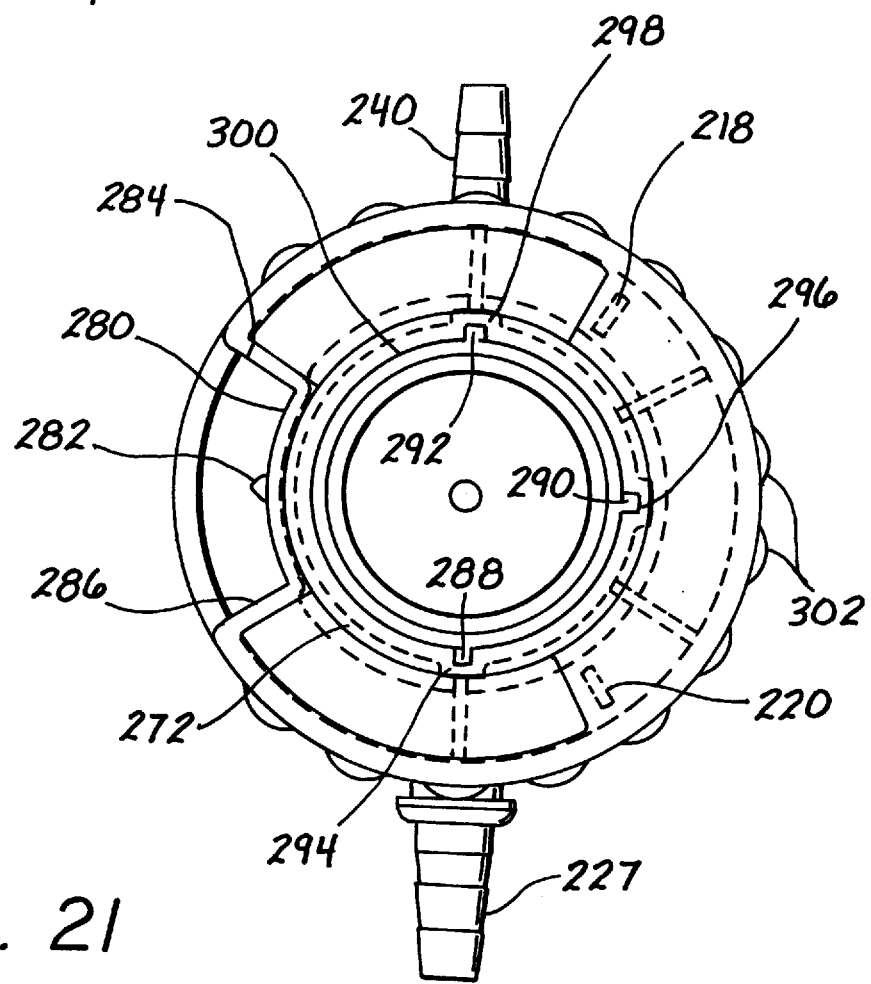
FIG. 21 shows a plan view of the valve of FIG. 16 with the underlying parts shown in outline.
Figure 22:
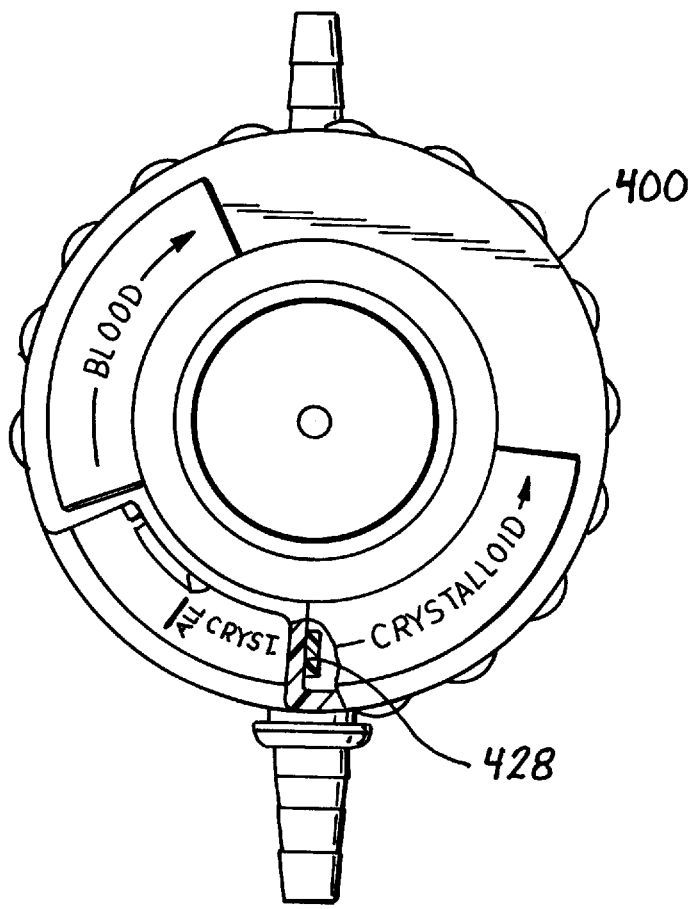
FIG. 22 shows a front view of another embodiment of the variable ratio valve.
Figure 25:
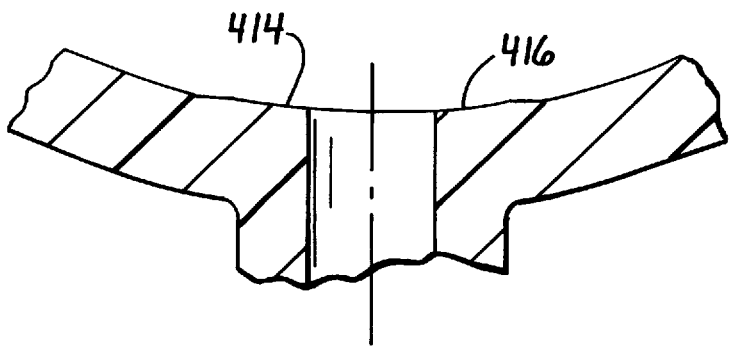
FIG. 25 shows an enlarged detail of the valve body adjacent the inlet port.

As shown in FIG. 21, three spaced apart side ribs or flanges 288, 290, and 292 on the exterior wall of valve core member 252 are received in three slots or notches 294, 296, and 298 around the central opening 300 of collar 270. The ribs or flanges 288, 290, and 292 when seated within the slots 294, 296, and 298 cause the core member 252 to rotate with the collar 270.

Around the periphery of the collar 270 are a plurality of knobs or rounded ribs 302. The knobs or rounded ribs 302 provide ease in grasping the collar 270 for rotating the collar 270 and the core member 252 to give the desired ratio of blood to crystalloid solution. The actual ratio is displayed on the monitor 80 as determined by flow through the venturi flow cells 30 and 36 and corresponding to the signals sent from the transducers 38, 40, 46 and 48 to the monitor 80.

The design of the variable ratio valve 58 ensures that each side of the valve will shut off to allow no flow as well as to provide adequate resolution during use so that the blood to crystalloid ratio can be adjusted at various flow rates.

Figure 23:
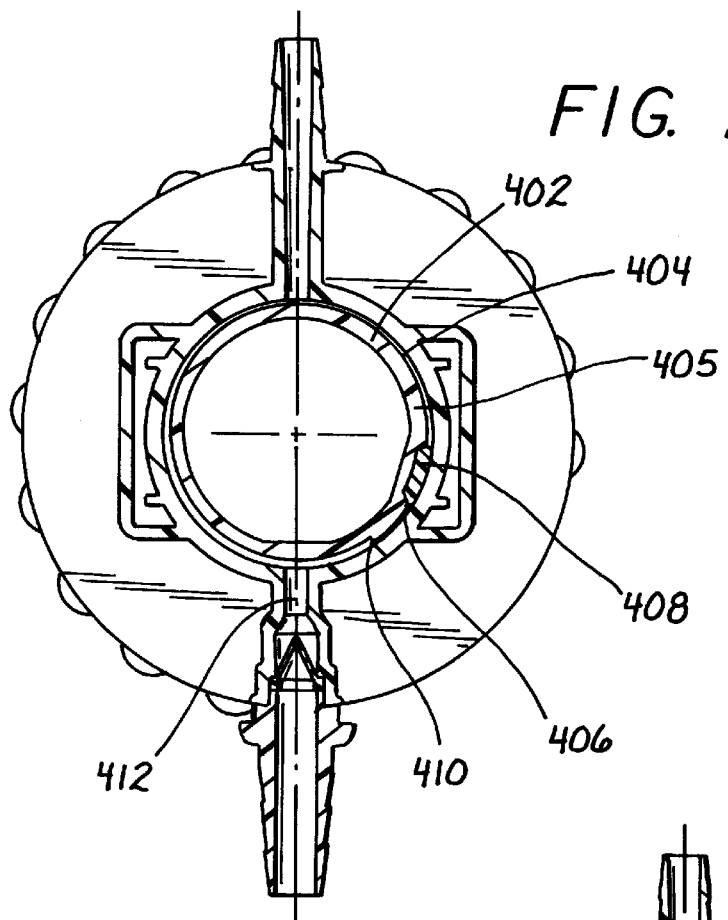
FIG. 23 shows a section through the valve of FIG. 22 taken through the crystalloid inlet port.

Another embodiment of the variable ratio valve 58 is shown in FIGS. 22, 23, 24 and 25. As shown, the valve 400 has a similar construction to valve 58 and like parts are labeled the same. The main difference is in the configuration of the core 402 and the valve body 404. As can be seen in FIG. 23, the valve core 402 has a cam or band surface 405 with a depression or recess 406 therein. Within the recess or depression 406 is disposed a plug 408 made of a material which is softer than the material of the core 402 or the cam 405.

Also, the cam or band 405 has an offset or shoulder 410 formed within the surface of the cam or band 405. The inlet port 412 for crystalline solution is detailed in FIG. 26. Here it can be seen that the valve body 405 in the region of the inlet port has a slightly projecting flattened curve area 414 and 416 on either side of the inlet port 412. The curve area 414 and 416 is adapted to receive the plug 408 when the cam or band 405 is rotated to bring the plug 408 opposite the inlet port 412.

Figure 24:
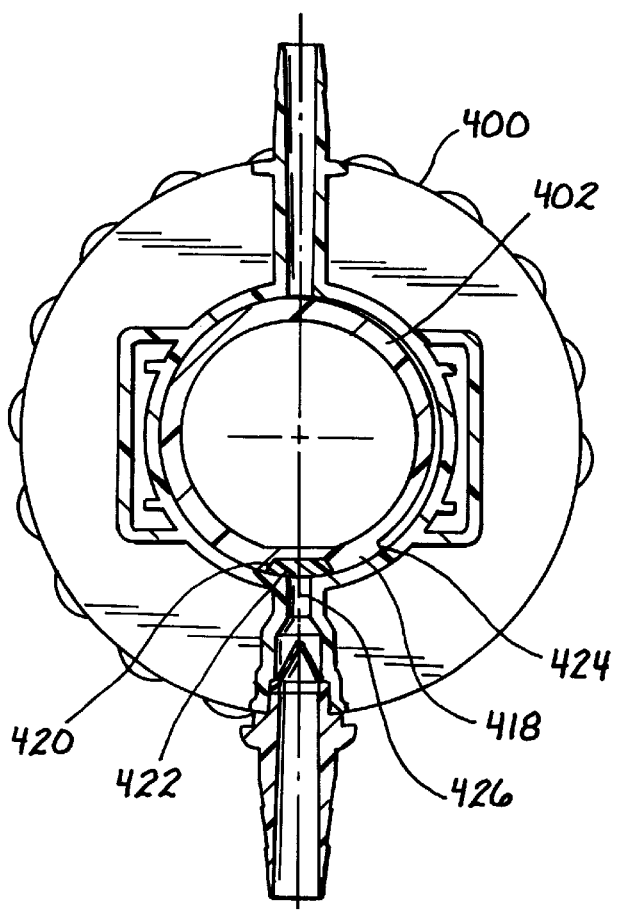
FIG. 24 shows a section through the valve of FIG. 22 taken through the blood inlet port.

Similarly, as can be seen in FIG. 24, the valve core 402 has a cam or band surface 418 with a depression or recess 420 therein. Within the recess or depression 420 is disposed a plug 422 made of a material which is softer than the material of the core 402 or the cam 418.

Also, the cam or band 418 has an offset or shoulder 424 formed within the surface of the cam or band 418. The inlet port 426 for is blood shown in FIG. 24. Here it can be seen that the valve body 405 in the region of the inlet port 426 also has a slightly projecting flattened curve area 414 and 416 on either side of the inlet port 426 as shown in FIG. 26. The curve area 414 and 416 is adapted to receive the plug 422 when the valve core 402 is rotated to bring the cam or band 418 with the plug 422 opposite the inlet port 426 for blood.

Another feature of the variable ratio valve 400 is that the cam or band surfaces 405 and 418 have a different lobe shape as they function over a sweep of 288 degrees instead of 180 degrees. Also, rotation of the valve core 402 is stopped by a single detent 428 which lies in a plane bisecting inlet ports 412 and 426. The shoulder or offset areas 410 and 424 allow for a slightly increased gap between the valve core 402 and the valve body 405 which allows for easier priming.

While the variable ratio valves 58 and 400 are shown with two inlets, more inlets can be incorporated to provide more than two different fluids. Similarly, additional cam or band surfaces can be incorporated into the valve core member 252 or 402 to admit variable amounts of additional fluids.

Preferably, the venturi flow cells 30 and 36, the transducers 38, 40, 46, and 48, and the variable ratio valve 58 are made of a clear plastic such as polyvinylchloride or polycarbonate. Other plastics can be used which are approved for medical use. Clear plastic is preferred for convenience in observing the flow of blood or crystalloid solution through the cells 30 and 36.

The variable ratio valve 400 preferably is made of a clear, polycarbonate or other hard, rigid material with the plugs 408 and 422 preferably being made of a softer plastic such as polyethylene to ensure a good seal.

For the same reasons, clear plastic tubing is preferred to permit observation of liquid flow through the tubing.

The system as described can be used to provide a range of flow of from 0 ml to 250 ml per minute for the crystalloid solution and a range of flow of from 0 ml to 500 ml per minute for the blood. Best results are obtained with the pump 62 being operated at no more than 70 revolutions per minute.

The blood parameters can be controlled within a wide range. Preferably, the hematocrit is kept in the range of from 15% to 35% by volume and the temperature is kept in the range of 18° C. to 42° C.

The crystalloid solution parameters can be controlled within a wide range. Preferably, the dynamic viscosity is kept in the range of from 19 to 26 centipoises (salt water±15%) and the temperature is kept in the range of 0° C. to 42° C.

For clinical use, the flow rate measurement is accurate to±5% (Full Scale Output) for blood or crystalloid.

The dimensions and designs of the individualized venturi flow cells, transducers, autovents, tubing, and variable ratio valve optimize the flow characteristics of the two fluids, blood and crystalloid solution while ensuring sufficient pressure drop across the venturi flow cells 30 and 36 to permit detection with standard high definition pressure monitoring equipment. At the same time, the designs and dimensions avoid creating shear forces which would cause destruction of red blood cells (hemolysis).

Various modifications of the invention are contemplated which will be obvious to those skilled in the art and can be resorted to without departing from the spirit and scope of the invention as defined in the following claims.

We claim:

1. An assembly for administering cardioplegia comprising in combination:
    at least one venturi flow cell for blood;
    at least one venturi flow cell for crystalloid solution;
    at least one means for connecting a crystalloid solution for flow through said at least one venturi flow cell for crystalloid solution;
    at least one means for connecting a source of blood for flow through said at least one venturi flow cell for blood;
    each said at least one venturi flow cell for blood and said at least one venturi flow cell for crystalloid solution comprising:
        a tubular member;
        a constriction formed within said tubular member to divide said tubular member into a convergent portion and a divergent portion;
        a first port in communication with said convergent portion of said tubular member;
        a second port in communication with said constriction;
        at least one transducer connected to said first port and to said second port for detecting a pressure drop between said first port and said second port respectively when crystalloid solution is caused to flow through said at least one venturi flow cell for crystalloid solution and when blood is caused to flow through said at least one venturi flow cell for blood; and,
    means for self-venting of gases from said transducers comprising;
        at least one second chamber;
        at least one gas permeable membrane dividing said at least one second chamber into at least one upper cavity and at least one lower cavity;
        at least one opening within said at least one upper cavity for self-venting gases to ambient;
        at least one conduit means disposed between said at least one lower cavity of said at least one second chamber and said at least one first compartment of said at least one first chamber; and,
    at least one one-way valve disposed within said conduit means for passage of gases from said at least one first compartment of said at least one first chamber, through said at least one one-way valve into said at least one lower cavity of said at least one second chamber for self-venting through said at least one gas permeable membrane.

2. An assembly according to claim 1 further comprising:
    a housing for securing said at least one venturi flow cell for crystalloid solution and said at least one venturi flow cell for blood and said at least one means for detecting a pressure drop.

3. An assembly for administering cardioplegia according to claim 1 wherein said at least one second chamber further comprises:
    at least one cap member overlying said at least one conduit means within said at least one lower cavity of said second chamber;
    at least one opening within said at least one cap member for passage of gas from said at least one conduit into said at least one lower cavity;
    at least one top member having at least one cup member extending inwardly from said at least one top member into said at least one upper cavity;
    at least one opening within said at least one cup member for self-venting gases from said at least one upper cavity to ambient;
    at least one base member, said at least one gas permeable membrane separating said at least one top member from said at least one base member; and,
    a plurality of ribs on the interior surface of at least one of said at least one top member and said at least one base member.

4. An assembly according to claim 1 wherein at least one of said venturi flow cells and said transducers is made of a plastic.

5. An assembly according to claim 1 wherein:

said transducers have communication means for transmission of data to a microprocessor.

6. An assembly according to claim 5 wherein:

said means for communication with a microprocessor include separable connection means.

7. An assembly for cardioplegia delivery according to claim 1 wherein:

said at least one venturi flow cell for flow of blood or crystalline solution therethrough has a throat sized to ensure that a pressure drop across the throat is sufficient for detection by said at least one means for detecting a pressure drop.

8. An assembly for cardioplegia delivery according to claim 7 wherein:

said at least one venturi flow cell for flow of blood or crystalline solution therethrough is further sized to optimize flow of the blood or crystalline solution through the throat.

* * * * *